(12) United States Patent
De Neve et al.

(10) Patent No.: US 10,548,542 B2
(45) Date of Patent: Feb. 4, 2020

(54) RADIOTHERAPY BOARD AND COUCH

(71) Applicant: Universiteit Gent, Ghent (BE)

(72) Inventors: Wilfried De Neve, Opwijk (BE);
Bruno Speleers, Beveren-Leie (BE);
Bert Boute, Ghent (BE); **Liv
Veldeman**, Oudegem (BE)

(73) Assignee: Universiteit Gent, Ghent (BE)

( * ) Notice: Subject to any disclaimer, the term of this patent is extended or adjusted under 35 U.S.C. 154(b) by 163 days.

(21) Appl. No.: 15/125,808

(22) PCT Filed: Mar. 24, 2015

(86) PCT No.: PCT/EP2015/056176
§ 371 (c)(1),
(2) Date: Sep. 13, 2016

(87) PCT Pub. No.: WO2015/144654
PCT Pub. Date: Oct. 1, 2015

(65) Prior Publication Data
US 2017/0028218 A1    Feb. 2, 2017

(30) Foreign Application Priority Data
Mar. 24, 2014   (EP) .................................... 14161326

(51) Int. Cl.
*A61B 6/04*   (2006.01)
*A61G 13/12*   (2006.01)
(Continued)

(52) U.S. Cl.
CPC ............ *A61B 6/0435* (2013.01); *A61G 13/08* (2013.01); *A61G 13/129* (2013.01);
(Continued)

(58) Field of Classification Search
CPC ....... A61B 6/04; A61B 6/0407; A61B 6/0435; A61G 13/00; A61G 13/08; A61G 13/12;
(Continued)

(56) References Cited

U.S. PATENT DOCUMENTS 5,289,520 A * 2/1994 Pellegrino ............ A61B 6/0435
378/208
8,374,312 B2 * 2/2013 Mansfield ............ A61B 6/0414
378/20
(Continued)

FOREIGN PATENT DOCUMENTS

WO    2013/139713 A1    9/2013

OTHER PUBLICATIONS

Mulliez et al. (Aug. 1, 2013) "Hypofractionated whole breast irradiation for patients with large breasts: a randomized trial comparing prone and supine positions," Radiother. Oncol. 108(2):203-208.

(Continued)

*Primary Examiner* — David R Hare
(74) *Attorney, Agent, or Firm* — Lathrop Gage LLP; James H. Velema, Esq.

(57) ABSTRACT

Provided herein is a radiotherapy breast board and couch for use in radiotherapy treatment of breast cancer patients, which are particularly suitable for treating the patient to the breast/thoracic wall and regional lymph nodes in prone position. The radiotherapy breast board and couch comprises a caudal part for supporting the lower body of the patient and a cranial part with supports for the head and non-treated parts of the upper body. The board or couch further provides an opening allowing for the affected breast of the patient to pass through and an opening allowing for the regional lymph nodes to pass trough as said patient lies in a prone position on said board or couch. This opening (Continued)

allows the use of a variety of beam directions to reach the affected region via short radiological path lengths without passing elements of the breast board or couch.

22 Claims, 18 Drawing Sheets

(51) Int. Cl.
*A61N 5/10* (2006.01)
*A61G 13/08* (2006.01)

(52) U.S. Cl.
CPC ........... *A61G 13/1295* (2013.01); *A61N 5/10* (2013.01); *A61G 2210/50* (2013.01); *A61N 2005/1097* (2013.01)

(58) Field of Classification Search
CPC .............. A61G 13/1205; A61G 13/121; A61G 13/1215; A61G 13/122; A61G 13/1235; A61G 13/1255; A61G 13/128; A61G 13/129; A61G 13/1295; A61G 2210/50; A61N 2005/1095; A61N 2005/1097; A61N 5/10
See application file for complete search history.

(56) References Cited

U.S. PATENT DOCUMENTS

| | | | | |
|---|---|---|---|---|
| 2003/0031301 A1* | 2/2003 | Longton | ................. | A61B 6/04 378/209 |
| 2004/0034932 A1* | 2/2004 | Zacharopoulos | ........ | A61B 6/04 5/601 |
| 2004/0081273 A1* | 4/2004 | Ning | ..................... | A61B 6/032 378/37 |
| 2004/0088791 A1* | 5/2004 | Corbeil | ................ | A61B 5/0091 5/601 |
| 2004/0103477 A1 | 6/2004 | Gagnon et al. | | |
| 2004/0111801 A1* | 6/2004 | Marin | .................. | A61B 5/0091 5/621 |
| 2004/0171933 A1* | 9/2004 | Stoller | ................. | A61B 6/0435 600/427 |
| 2007/0033735 A1* | 2/2007 | Formenti | ............. | A61B 6/0414 5/600 |
| 2008/0005841 A1* | 1/2008 | Zelnik | .................... | A47C 20/00 5/601 |
| 2008/0043905 A1* | 2/2008 | Hassanpourgol | .... | A61B 6/0414 378/37 |
| 2008/0201850 A1* | 8/2008 | Brito | ................... | A61B 6/0414 5/601 |
| 2009/0080594 A1* | 3/2009 | Brooks | .................. | A61B 6/502 378/4 |
| 2013/0019876 A1 | 1/2013 | Zacharopoulos et al. | | |
| 2013/0198960 A1* | 8/2013 | Angott | .................. | A61B 5/702 5/622 |
| 2013/0340766 A1* | 12/2013 | Seger | ..................... | A61G 99/00 128/845 |
| 2014/0058286 A1* | 2/2014 | DeFreitas | ........... | A61B 6/0435 600/567 |

OTHER PUBLICATIONS

International Preliminary Report on Patentability corresponding to International Patent Application No. PCT/EP2015/056176, completed Jun. 20, 2016.
International Search Report with Written Opinion corresponding to International Patent Application No. PCT/EP2015/056176, dated Jul. 6, 2015.

* cited by examiner

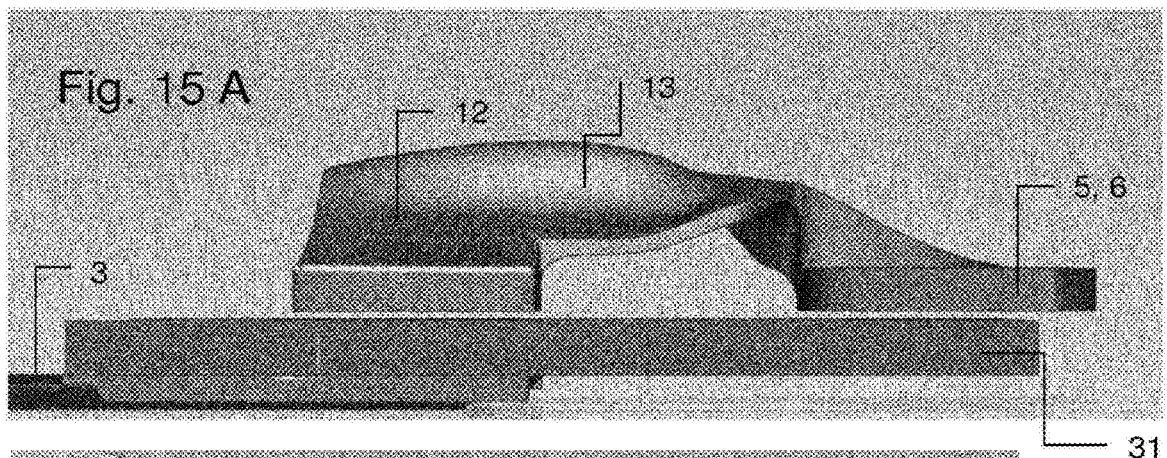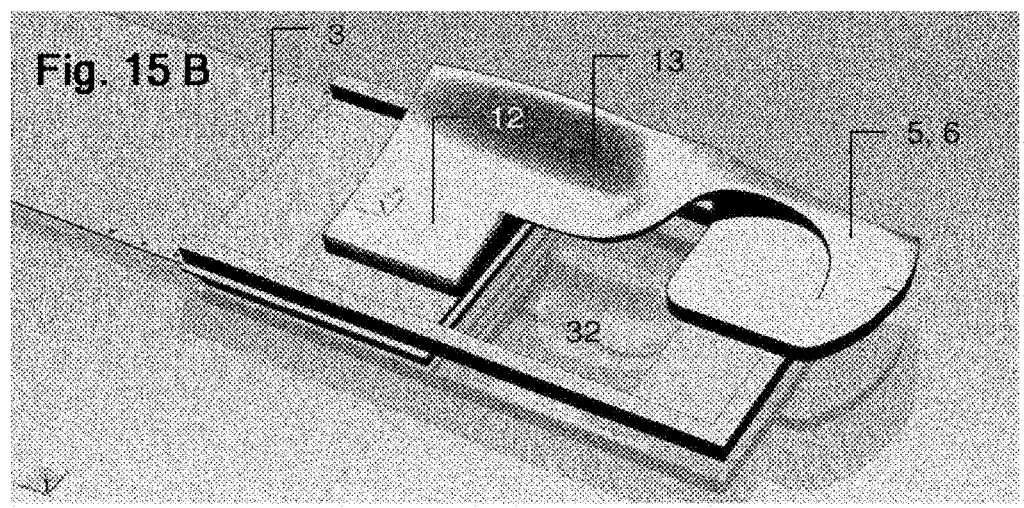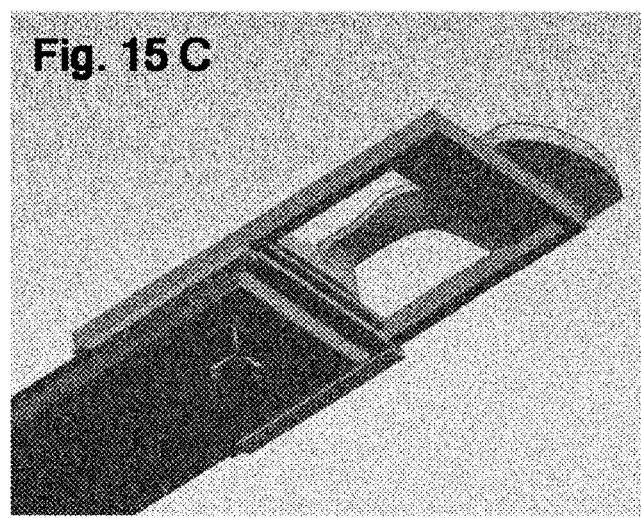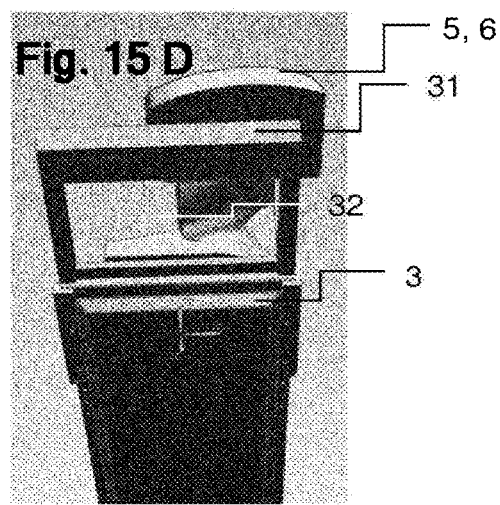

RADIOTHERAPY BOARD AND COUCH

RELATED APPLICATIONS

This application is a 35 U.S.C. § 371 filing of International Application No. PCT/EP2015/056176, filed Mar. 24, 2015, which claims priority to European Patent Application No. 14161326.5, filed Mar. 24, 2014, each of which is incorporated herein by reference in its entirety.

FIELD OF THE INVENTION

Provided herein is a breast board and couch for use in radiotherapy treatment of breast cancer patients, which is particularly suitable for treating the patient to the breast/thoracic wall and its regional lymph nodes in prone position.

BACKGROUND OF THE INVENTION

Radiotherapy, e.g. after breast-conserving surgery improves loco-regional control and survival, however at the risk of cardiac events and secondary cancer of the lungs and the non-treated breast. In view thereof, there is an increased tendency for treating patients in prone position instead of the traditional treatment in supine position. Indeed, the treatment in prone position can result in a reduced acute toxicity and a reduced risk of radiation-induced cardiac toxicity, lung and contra-lateral breast cancer. Prone positioning exploits gravitation to obtain its radio-physical advantages. The downwards hanging breast elongates vertically, narrows horizontally, stretches skin folds and moves target tissue away from radiation-sensitive organs, mainly the heart and lungs.

A number of devices for prone breast irradiation is currently available. A first category includes prone breast boards, which are placed on top of the standard treatment couch surface in support of the patient lying prone. A further category of devices includes prone breast couches, which replace the standard treatment couch blade or part thereof. Prone breast boards or couches feature a specifically shaped aperture, thereby allowing the breast to hang freely below the board or couch surface.

Examples of such prior art breast couches are disclosed e.g. in PCT application WO20013/139713 and US patent application US 2013/019876. Both breast couches however require that at least the ipsilateral arm at the side of radiation treatment of the patient is positioned above or behind the head, which causes a lot of discomfort for patients having undergone breast or lymph node surgery.

In practice, the use of currently available prone breast boards and prone breast couches is limited to patients requiring breast-only irradiation. However, about one third of the patients require irradiation of the breast and the regional lymph node regions. For these patients, the above-mentioned prone breast boards or couches are unsatisfactory. US patent application US2004/105477 for example discloses a breast board, having one or two apertures configured to for the breast(s) to be pendently suspended therethrough, with no radiation beam access to the lymph nodes. Furthermore, such a board may severely restrict the range of favourable beam access and disturb radiation build-up needed to protect the skin.

Thus, there is a need for radiotherapy breast boards or couches which mitigate one or more of the problems stated above.

SUMMARY OF THE INVENTION

Provided herein is a breast board and breast couch for use in radiotherapy treatment of breast cancer patients, which can allow for treating the breast and the regional lymph nodes (axillary, internal mammary, infra- and supra-clavicular lymph nodes) of a patient in prone position.

As used herein, the term "breast board" intends to describe a board that can be positioned to rest on an existing support, such as an imaging and/or radiotherapy table or an imaging and/or radiotherapy couch-top or blade e.g. fixed to a pedestal.

The term "breast couch" intends to describe a self-supporting article, which is connected to a patient support system such as a pedestal or robotic arm, or to an existing radiotherapy couch blade and which replaces at least part of said couch blade, thereby creating open space underneath the couch.

As an intermediate between the self-supporting breast coach and the supported or resting breast board, the breast board as defined in any one of the embodiment herein, can be supported on a frame (31) rather than on a radiotherapy table top or blade (3).

The idea is to use the radiotherapy breast board on e.g. a standard imaging couch or table, for determining and simulating the exact position of the patient in need of receiving radiotherapy. This position can then be replicated on the self-supporting breast couch prior to applying the radiotherapy, thereby giving free access of the radiation beam to the breast and lymph nodes to be treated.

More particularly, in a first aspect, the present invention relates to a radiotherapy breast couch for supporting a patient in prone position, essentially configured in three different ways: with a symmetrical or asymmetrical supported structure, or as an asymmetrical self-supporting structure.

Said three types of breast couches share the following common properties in that they all comprise:

- a longitudinal body supporting member (12, 13), configured for supporting the non-treated side of the patient's body, including a surface or wedge (13) to support the contralateral breast, comprising an anchorage structure (4) for connecting the support member (12, 13) to a radiotherapy couch blade (3) or pedestal (2), and a head support (5, 6), configured to support the head of the patient;
- a longitudinal first arm supporting member (11), configured for supporting the ipsilateral arm of said patient at the side of treatment (23) of the patient, wherein said ipsilateral arm is held backwards, alongside the body; and
- optionally a second arm supporting member (16, 17, or 18) attached to the body supporting member (12) and/or head support (5, 6), configured to support the arm and eventually the shoulder of the patient at the non-treated side (contralateral arm);
- wherein the body supporting member (12, 13) and the first arm supporting member (11) are mutually arranged to provide an aperture or air gap for protrusion of the breast (22) and the regional lymph nodes undergoing treatment therethrough, while said patient lies in prone position on said breast couch. Note that said first arm support is not connected to the head support, increasing freedom of the radiation beam access. Said longitudinal first arm support is hence positioned parallel to the body support in a caudal-cranial orientation. Said longitudinal first arm support is typically connected to the caudal part of the breast couch only.

In a second aspect, the invention provides for a radiotherapy breast board for supporting a patient in prone position, which is suitable for being placed on a table top, frame, or blade of a radiotherapy or imaging table or couch, supporting a patient in need of breast tumor radiotherapy in prone position.

Said breast board comprises:

- a longitudinal body supporting member (12, 13), configured for supporting the non-treated side of the patient's body, including an inclined surface or wedge (13) to support the contralateral breast, comprising
- a head support (5, 6), configured to support the head of the patient;
- a longitudinal first arm supporting member (11), configured for supporting the ipsilateral arm of said patient at the side of treatment (23) of the patient, wherein said ipsilateral arm is held backwards, alongside the body; and
- optionally a second arm supporting member (16 or 17) attached to the body supporting member (12) and/or head support (5, 6), configured to support the arm of the patient at the non-treated side (contralateral arm);

wherein the body supporting member (12, 13) and the first arm supporting member (11) are mutually arranged to provide an aperture or air gap for protrusion of the breast (22) and the regional lymph nodes undergoing treatment therethrough, while said patient lies in prone position on said breast couch. Also here, said first arm support is not connected to the head support, increasing freedom of the radiation beam access. Said longitudinal first arm support is hence positioned parallel to the body support in a caudal-cranial orientation. Said longitudinal first arm support is typically connected to the caudal part of the breast board only.

Below, each of the three types of couches is highlighted in more detail:

1) The Symmetric Supported Structure (Cf. FIGS. 1 and 2)

The symmetric supported radiotherapy breast couch comprises:

- a caudal anchorage structure (4) suitable for connecting the prone breast couch (II) to a radiotherapy patient support system (I). Typically, this patient support system is the caudal part of a couch blade (3) or the pedestal (2). Alternatively, robotic arms are increasingly used as patient support systems and the anchorage structure can hence be designed to connect to such a robotic arm as well. Standard anchoring mechanisms can be used, that are compatible with commercially existing table blades, pedestals or robotic arms;
- a cranial part (5) comprising a head support (6). The head support being adjustable to the patient's anatomy in the lateral, and cranio-caudal direction and optionally rotatable alround left-right and longitudinal axes. Optionally, the head support can be slightly elevated in order to better fit the patient's anatomy or to increase comfort. Optionally, the head of the patient can be fixed by a preferably patient-specific thermoplastic facemask.
- one, or a pair of opposed lateral frame member(s) (7, 8), preferably configured as bent arms, such as C-arms, which are allowed to rotate along a longitudinal axis (cf. FIG. 1A-C), connecting said anchorage structure (4) and said cranial part (5). In a preferred embodiment, each frame member comprising a bent bar (e.g. a C-arm) which is connected via e.g. a pivot (9, 10) bearing to said anchorage structure at a first end and to said cranial part at a second end;
- a longitudinal body supporting member (12) comprising a surface or wedge (13) configured for supporting the non-treated side of the patient's body including the contralateral breast, connected to the anchorage structure and the cranial part (5) or head support (6). Typically said body supporting member is supported (carried) by the one or more frame members;
- a first arm supporting member (11) positioned parallel to, or between said frame one or more frame member(s) and connected to said anchorage structure, configured for supporting a first stretched or bent arm of said patient positioned alongside the patient's body or back. Typically said first arm supporting member is supported (carried) by the one or more frame members. The first arm supporting member (11) is preferably composed out of a through or half-tube-like structure supporting the first stretched or optionally curved arm starting from the wrist and ending just below the humeral head of said patient positioned alongside the patient's back or body. The shoulder and breast area is completely free increasing the range of favorable beam access to treat the breast and the regional lymph nodes in prone position. A set of standard wedges can be made to match the individual patient's anatomy. At extreme anatomical abnormalities individual body and arm/shoulder supporting members can be made which are adapted to the patient's anatomy.

The breast couch can optionally comprise one or more additional arm support(s) (16) positioned on the head support for supporting a second arm of said patient positioned near and behind or above the patient's head.

The breast couch can optionally comprise one or more additional arm support(s) (not shown on FIGS. 1A-C) positioned on the head support or anchorage structure for supporting the first arm of said patient positioned near and behind or above the patient's head, thereby removing the need of having the first longitudinal arm support (11).

The body supporting member (12), or its wedge (13) supporting the non-treated or contralateral breast can be constructed out of optically transparent and/or radiolucent material e.g. polycarbonate or PETG, enabling easy monitoring of the radiation beam and ensuring it will not hit the non-treated breast or other body parts which are not to be irradiated.

Preferably, the symmetric frame can be used both for left and right-tailed breast patients, whereby the supports that have appropriate symmetry (11, 14, 15) can be moved and swapped to the other side of the couch. Other unilateral anatomical supports (12, 13) must be specifically constructed for left- or right-sided use.

In all embodiments, the breast couch provides an opening allowing the breast to be treated to pass through the couch when lying in prone position on said couch. Preferably, said opening is wide enough, so as to allow for the regional lymph nodes to be available for radiation therapy.

2) The Asymmetrical Supported Breast Couch

The asymmetric supported radiotherapy breast couch comprises the same characteristics as the symmetrical supported couch but under construction of an asymmetrical design (FIG. 2B). The head support unit (5, 6) is connected to a unilateral suspension frame member (8). At its caudal end, the suspension frame (8) is connected to the anchorage structure (4). The body supporting member (12) and its wedge (13) are connected to the head support unit (5, 6) cranially and to the anchorage structure (4) caudally and may, optionally, be connected to the suspension frame member (8). At the side of the breast to be treated, the first arm support (11) is connected to the anchorage structure (4) through a, preferentially movable, support member (8'). Said first arm support is hence not connected to the cranial head support, but only to the caudal anchorage structure, The asymmetrical supported breast couch exists in two copies which look like left-right mirror images of each other: one for left-tailed breast patients and one for right-tailed breast patients, respectively. The asymmetrical design of the breast couch allows slim construction of the body and arm supporting members to secure large free space towards the nozzle of the gantry that is turning around the patient during treatment. The free space can be exploited to position the isocenter of the gantry far off the sagital midplane of the patient, for example laterally inside the treated breast. With increasing the distance between the isocenter and the sagital midplane the range of favourable non-coplanar beam directions increases (cf. FIG. 7), and allows irradiating the affected region without passing through elements of the breast couch.

3) The Asymmetrical Self-Supporting Prone Breast Couch (FIG. 3A-B) Comprising:

The asymmetrical fixed frame radiotherapy breast couch, or self-supporting radiotherapy breast couch, comprises largely the same characteristics as mentioned above for the supported breast board, with this difference that the lateral frame members are incorporated into the body supporting (12) and first arm supporting members (11). Also said self-supporting breast couch provides an opening allowing the breast to be treated to pass through the body supporting member as said patient lies in a prone position on said couch. Advantageously, also the regional lymph nodes are accessible for radiotherapy treatment of the patient lying in prone position on said breast board or couch. The asymmetrical self supporting breast couch contains an asymmetrical self-supporting design. It hence contains two copies: one for left-tailed breast patients and one for right-tailed breast patients, respectively.

The cranial part of the breast couch of each of the three types explained above will have a rounded shape in contrast to other existing systems with a typical rectangular shape. This shape will increase the range of non co-planar beam access by reducing the collision risk between the table and the radiation nozzle or head part of the gantry. More particularly, the range of favourable beam access is increased, avoiding erroneous radiation build-up due to structural interference and hence protecting the skin of the area to be treated.

The asymmetrical design of the breast couch or board allows slim construction of the body and arm supporting members to secure large free space towards the nozzle of the gantry when turning around the patient during treatment. The free space can be exploited to position the isocenter of the gantry far off the sagittal midplane of the patient, for example laterally inside the treated breast. With increasing the distance between the isocenter and the sagittal midplane the range of favourable non-coplanar beam directions increases (FIG. 7), and allows irradiating the affected region without passing through elements of the breast board or couch.

The three different prone breast couch design characteristics as described above (asymmetric or symmetric supported, or asymmetric self-supporting) can also be embedded in the breast boards that are not anchored to a standard couch blade or a pedestal or robotic arm, but are positioned on top of existing couch blades or imaging tables. In essence, each breast board would have similar features as the corresponding breast couch, but without the typical anchorage structure for connecting it to a pedestal or robotic arm. Construction of boards is less challenging than construction of couches with equal design characteristics. Indeed, the structural strength of couches must allow extension in air from the anchorage points; supporting the full weight of the patient. As explained, breast boards use the structural strength of the couch blade or imaging table underneath. The position of such a breast board may be mimicking the positioning of the respective couch, by cushions or additional support members with predetermined angles. Of particular interest is the positioning of a breast board on top of a half-sided couch blade. By omitting the left or right half of the couch blade, beam access to the lymph node regions can be created without irradiating through the couch blade for left- or right-sided breast cancer, respectively. The half couch blade at the non-treated side supports the cranial part of the board. This would e.g. allow the production of a low-cost asymmetrical breast board, which can be used on an imaging table and an existing half-sided radiation couch blade, without the need for an complicated anchorage structure, or other adapting features.

The radiotherapy breast couches and boards described herein can be adapted such that the elements of the board and couch, in particular the frame members, do not block the beam path to the breast as well as the regional lymph nodes. Moreover, the boards or couches can allow for the patient to lie on the board or couch with at least the ipsilateral arm positioned alongside the patient's body. As a result thereof, the present radiotherapy couches enable radiotherapy of the breast and regional lymph nodes in prone position allowing a single patient set-up, thereby preventing pain and discomfort experienced by the patient while moving to different positions during radiotherapy.

Moreover, the position with the ipsilateral arm alongside the body typically causes less discomfort and pain to the patient, compared to standard prone radiotherapy procedures wherein the patient is positioned with two elevated arms, or with the ipsilateral arm being elevated. It is noted that patients receiving radiotherapy of the breast or lymph node area often previously underwent surgery of the axilla, resulting in restricted mobility of the shoulder, as well as pain and discomfort when elevating the arm(s).

Using a prototype of the breast board or couch as defined herein, the inventors have shown that the radiation beam access range is much higher than with reference radiation therapy couches, enabling the use of such a couch for much more precise radiotherapy of e.g. whole and partial breast, with or without lymph node involvement. In addition, preliminary tests have indicated that the collateral radiation dosage (e.g. in the heart, lungs etc,) can be seriously reduced by using the radiotherapy board or couch as defined herein. Due to its highly adjustable conformation, the breast board or couch as defined herein has near-anatomic dimensions, that can ideally be tailored for each patient, increasing the comfort for the patient during the radiation enormously.

The above and other characteristics, features and advantages of the concepts described herein will become apparent from the following detailed description, which illustrates, by way of example, the principles of the invention.

The invention hence provides for the following aspects:

Aspect 1. A radiotherapy breast couch for supporting a patient in need of breast tumor radiotherapy in prone position, comprising:

a longitudinal body supporting member, configured for supporting the non-treated side of the patient's body, including the contralateral breast, comprising an anchorage structure for connecting the support member to a radiotherapy couch, pedestal or robotic arm, and a head support, configured to support the head of the patient;

a longitudinal first arm supporting member, configured for supporting the arm of said patient at the side of treatment of the patient (ipsilateral arm), wherein said arm is positioned backwards alongside the body; and optionally a second arm supporting member attached to the body supporting member or head support, configured to support the arm of the patient at the non-treated side;

wherein the body supporting member and the first arm supporting member are mutually arranged to provide an air gap for protrusion of the breast and the regional lymph nodes undergoing treatment therethrough, while said patient lies in prone position on said breast couch. Said ipsilateral arm is hence stretched or bent backwards alongside the patient's body, hip, or back. Said longitudinal first arm support is hence positioned parallel to the body support, extending in the caudal-cranial direction. Typically, said longitudinal first arm support is only connected to the caudal region of the radiotherapy breast couch.

Aspect 2. A radiotherapy breast board suitable for being placed on, or attached to, a table top, frame, or blade of a radiotherapy or imaging table or couch, for supporting a patient in need of breast tumor radiotherapy in prone position, comprising:

a longitudinal body supporting member, configured for supporting the non-treated side of the patient's body, including the contralateral breast;

a head support, configured to support the head of the patient;

a longitudinal first arm supporting member, configured for supporting the arm of said patient at the side of treatment of the patient (ipsilateral arm), wherein said arm is positioned backwards alongside the body; and optionally a second arm supporting member attached to the body supporting member or head support, configured to support the arm of the patient at the non-treated side;

wherein the body supporting member and the first arm supporting member are mutually arranged to provide an air gap for protrusion of the breast and the regional lymph nodes undergoing treatment therethrough, while said patient lies in prone position on said breast board. Said ipsilateral arm is hence stretched or bent backwards alongside the patient's body, hip, or back. Said longitudinal first arm support is hence positioned parallel to the body support extending in the caudal-cranial direction. Typically, said longitudinal first arm support is only connected to the caudal region of the radiotherapy breast board.

Aspect 3. The radiotherapy breast couch or board according to aspect 1 or 2, wherein said body supporting member comprises a wedge, configured for receiving the contralateral breast.

Aspect 4. The radiotherapy breast couch or board according to anyone of aspects 1 to 3, wherein said body supporting member comprises a wedge which is radiolucent or translucent.

Aspect 5. The radiotherapy breast couch or board according to anyone of aspects 1 to 4, wherein said body supporting member comprises a hole allowing the contralateral arm of the patient to pass through.

Aspect 6. The radiotherapy breast couch or board according to anyone of aspects 1 to 5, wherein said first and second arm supporting members support the arms of the patient when in crawl, skeleton, or butterfly position.

Aspect 7. The radiotherapy breast couch or board according to anyone of aspects 1 to 6, wherein said second arm supporting member is attached to the head support and is configured to support the contralateral arm of the patient when positioned above or behind the patient's head.

Aspect 8. The radiotherapy breast couch or board according to anyone of aspects 1 to 7, wherein said head support additionally comprises an arm supporting member configured to support the arm of the patient at the side of treatment, when positioned above or behind the patient's head.

Aspect 9. The radiotherapy breast couch or board according to anyone of aspects 1 to 8, wherein said first and second arm supports are comprised out of one or more throughs, capable of supporting an arm.

Aspect 10. The radiotherapy breast couch or board according to anyone of aspects 1 to 9, wherein the position of said first arm support can be adjusted longitudinally, laterally, and/or vertically.

Aspect 11. The radiotherapy breast couch or board according to anyone of aspects 1 to 10, wherein the position of said second arm support can be adjusted longitudinally, laterally, and/or vertically.

Aspect 12. The radiotherapy breast couch or board according to anyone of aspects 1 to 11, wherein the first arm support has an inclination of between 0 and 35 degrees with respect to the body supporting member. Such an inclination allows the positioning of the ipsilateral arm backwards, the hand region being slightly elevated versus the shoulder region, enabling better beam access to the lateral breast region to be treated.

Aspect 13. The radiotherapy breast couch or board according to anyone of aspects 1 to 12, wherein said head support is adjustable to the patient's anatomy in cranio-caudal and/or lateral direction.

Aspect 14. The radiotherapy breast couch or board according to anyone of aspects 1 to 13, wherein said head support is adjustable in height or inclination.

Aspect 15. The radiotherapy breast couch or board according to anyone of aspects 1 to 14, wherein said head support is rotatable in the left-right position.

Aspect 16. The radiotherapy breast couch or board according to anyone of aspects 1 to 15, wherein the head of the patient can be fixated by a face-mask, such as a patient-specific, preferably thermoplastic face-mask.

Aspect 17. The radiotherapy breast couch according to anyone of aspects 1 to 16, wherein said body supporting member is self-supporting and connected to the patient-support system.

Aspect 18. The radiotherapy breast couch according to anyone of aspects 1 to 16, wherein said body supporting member and/or first arm supporting member is supported by one or more frame members connected via a pivot bearing to said anchorage structure at a first end and to the head support at a second end.

Aspect 19. The radiotherapy breast couch according to aspect 18, wherein said pivot bearings have an axis of rotation in the caudal-cranial direction.

Aspect 20. The radiotherapy breast couch according to aspect 18 or 19, wherein said frame members are bent bars, preferably C-shaped bent bars.

Aspect 21. The radiotherapy breast couch or board according to anyone of aspects 1 to 20, wherein said second arm support is removable or adjustable.

Aspect 22. The radiotherapy breast couch or board according to any one of aspects 1 to 21, wherein said first arm support is removable or adjustable.

Aspect 23. The radiotherapy breast couch or board according to any one of aspects 1 to 23, wherein said head support is adapted for rotation along one or more axes of rotation, selected from:

a normal axis running in the caudal-cranial direction; and
a lateral axis running in the left-right direction.

Aspect 24. A radiotherapy or imaging table comprising the breast board according to any one of aspects 1 to 23, placed on the table top, frame or blade of said radiotherapy table.

Aspect 25. A radiotherapy table comprising the breast couch according to any one of aspects 1 to 23, anchored to a patient support system, though its anchoring structure (4).

Aspect 26. The radiotherapy couch according to aspect 25, wherein said patient support system is pedestal or robotic arm.

Aspect 27. The radiotherapy couch according to any one of aspects 1 to 23, wherein said breast couch can be tilted upwards with respect to the anchorage means and/or patient support system to which it is connected, in order to facilitate the patients climbing on the board.

Aspect 28. A removable patient supporting device configured to fit under the radiotherapy couch according to anyone of aspects 1 to 23, to facilitate the patients positioning on the couch.

Aspect 29. The removable device according to aspect 28, which is positioned under the air gap formed by said body supporting member and the first arm supporting member.

Aspect 30. The removable device according to aspect 28 or 29, which is removably connected to the patient support system or to the radiotherapy breast couch.

Aspect 31. The removable device according to aspect 28 or 29, which is positioned on the floor. Preferably said device is a mobile structure between the head support and the first arm supporting member, to ensure safe positioning of the patient on said couch or board. In preferred embodiments, said structure is a removable device (28), e.g. presented on a floor-positioned trolley (29) with hydraulic arm (30), Aspect 32. The radiotherapy breast couch or board according to any one of aspects 1 to 23, additionally comprising a mesh or net between the head support and the first arm supporting member, to ensure safe positioning of the patient on said couch or board.

Aspect 33. The radiotherapy breast couch according to any one of aspects 1 to 23, which is connected to a table top, frame or blade via an anchoring system (4). In some embodiments like in FIG. 11, such an anchoring system, structure, or element (4) may comprise a base plate (4a), which can e.g. be attached to the table blade or the pedestal; a frame (4b) substantially perpendicular to the base plate, which can comprise a pivoting means such as a hinge or bearing (4c), and which is connected to one or more connector structure(s) (4e), each carrying one of the body supporting means (12 and 13 (not shown)) and the arm supporting means (11). In one specific embodiment, said frame and connector structure(s) can slide or translate sideward over a width regulatory rod or axis (4d). This sliding enables the adjustment of the width of the couch, or the space between the arm support (11) and the body support (12 and 13 (not shown)) and makes it adjustable to the patient's anatomy. In further embodiments, said pivoting means or bearing (4c) can also be used to make small position adjustments of the breast board.

Aspect 34. In one embodiment, a modular breast board or couch according to any one of aspects 1 to 23 is disclosed, comprising a body support (12, 13), which supports head, hemi-thorax, contralateral breast, contralateral arm and upper abdomen); an ipsilateral arm and shoulder support (11); a lower abdomen and upper leg support (14, 15) and an anchorage element (4). The anchorage element connects the three supports (11; 12 and 13 (not shown); and 15 (not shown)) to the pedestal, the couch blade, frame, or part thereof. The lower legs and feet of the subject can adequately be supported by standard commercial devices or cushions.

Aspect 35. The breast board according to any one of aspects 1 to 24, wherein said breast board is positioned or connected to a radiotherapy or imaging table frame (31) as shown in FIG. 15. This embodiment enables an increased radiation beam access range (32) from underneath the table, since only the frame of the table top is present. It also enables the use of a floor laser aimed at the breast of the patient, allowing more precise and reproducible latero-lateral patient positioning.

BRIEF DESCRIPTION OF THE DRAWINGS

The drawings depicted herein are merely for illustrative purposes and are not to be seen as limiting the invention in any particular way.

FIG. 8A is a top side perspective view of the presently disclosed breast board or couch illustrating the ability to move the arm supporting member (11). FIGS. 8B and 8C are diagrammatic views of a patient before and after placing an ipsilateral arm in the first arm support, respectively. As is shown in FIG. 8B versus 8C, the shoulder of the patient is moved backwards due to the positioning of the arm supporting member (11), which results in optimal shoulder extension and stretching of the skin, and optimal positioning of the breast and lymph nodes to be treated.

FIG. 10.

FIG. 15: FIG. 15A is a side elevation view of the breast board or couch of FIG. 1, FIG. 15B is a top, side perspective view thereof, FIG. 15C is a bottom, side perspective view thereof, and FIG. 15D is a bottom, front perspective view thereof. These figures show a schematic view of the breast board as defined herein positioned on a frame (31), placed on a radiotherapy table top (3), permitting free access (32) of the radiation beam released from under the radiation table. The breast board in this example comprises a body supporting member (12), comprising a wedge (13) and a head support (5, 6).

DETAILED DESCRIPTION OF THE INVENTION

Figure 1A:
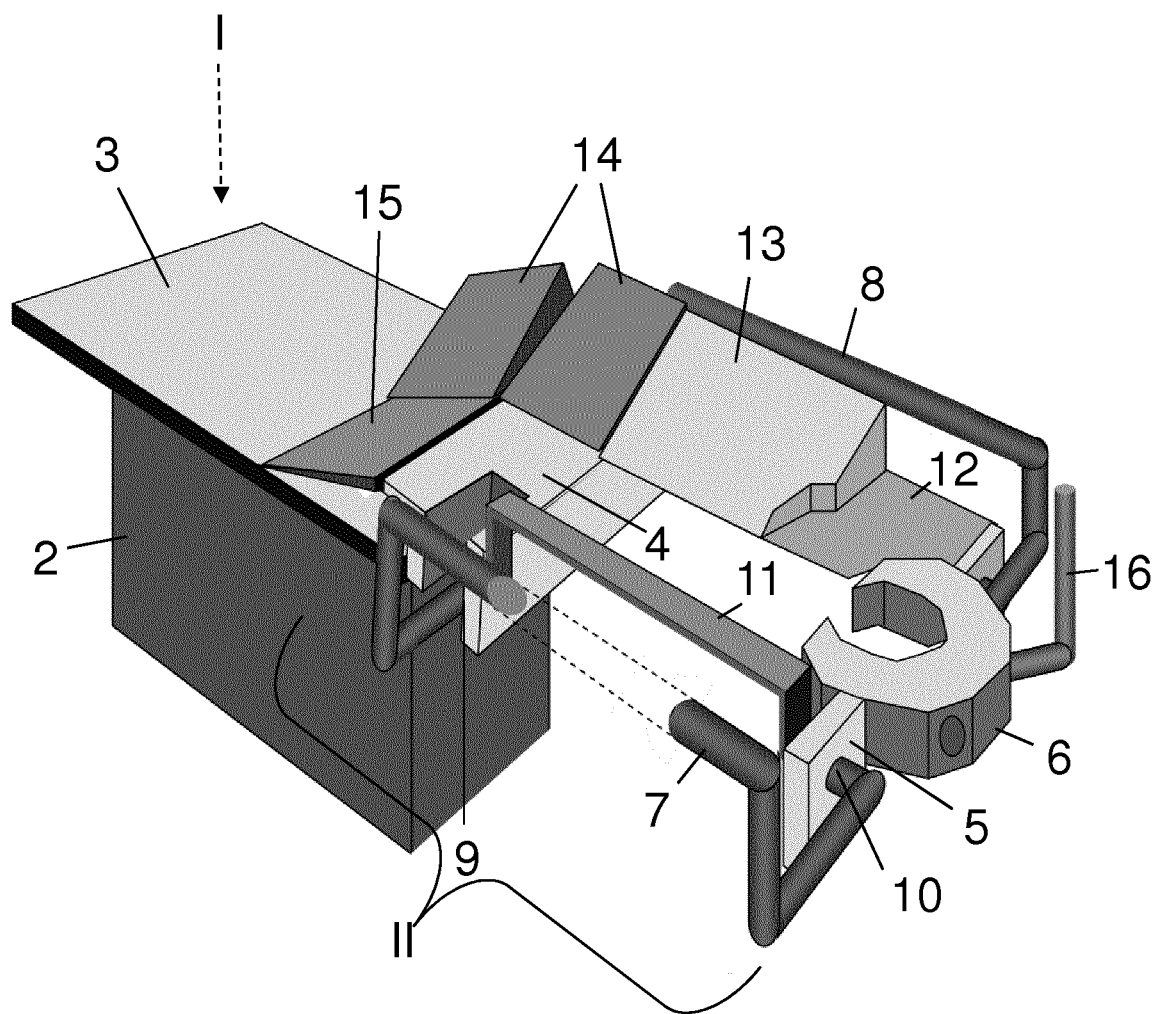
FIG. 1: Perspective view (A, B) and exploded view (C) of a particular embodiment of the radiotherapy table (I) to which a symmetrical C-arm supported breast couch (II) is attached as described in one of the embodiments herein. The radiotherapy table (I) comprises a base or pedestal (2) with the caudal part of a couch blade (3). The couch blade (3) provides connector devices for the anchorage structure (4) of the breast couch (II). The anchorage structure is connected to a cranial structure (5) having a head support (6) via one or more frame members, in this exemplary case C-arms (7, 8). Said one or more frame members (7, 8) are each connected to the anchorage structure (4) and the cranial structure (5) or head support via e.g. pivot bearings (9, 10). The radiotherapy couch can further comprise elements for supporting the patient, including an arm support (11), a body supporting member (12, 13), cushions (14), a slope element (15), and a further arm supporting member or handle (16).

While potentially serving as a guide for understanding, any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The values as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to ensure one or more of the technical effects envisaged herein. It is to be understood that each value as used herein is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the concepts described herein, including technical and scientific terms, have the meaning as commonly understood by one of ordinary skill in the art. By means of further guidance, definitions for the terms used in the description are included to better appreciate the teaching of the present disclosure. The terms or definitions used herein are provided solely to aid in the understanding of the teachings provided herein.

The term "regional lymph nodes" as used herein refers to lymph nodes neighbouring the breasts, particularly of the breast to be treated, more particularly to the axillary, internal mammary, infraclavicular and supra-clavicular lymph nodes neighbouring the breasts, particularly of the breast to be treated.

The term "longitudinal" as used herein refers to objects having an aspect ratio (length divided by width) of at least 2, preferably at least 4.

Reference throughout this specification to "one embodiment" or "an embodiment" means that a particular feature, structure or characteristic described in connection with the embodiment is included in at least one embodiment envisaged herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are also envisaged herein, and form different embodiments, as would be understood by those in the art. For example, in the appended claims, any of the features of the claimed embodiments can be used in any combination.

The term "skeleton" when used in combination with the indication of the patient's positioning on the breast couch or table refers to the position wherein both arms are positioned alongside the body. The term resembles the face down (prone) position used on a slide in the skeleton sports discipline.

The term "crawl" when used in combination with the indication of the patient's positioning on the breast coach or table refers to the position wherein one arm is positioned alongside the body and the other arm is positioned above the head. The term resembles the alternating arms movement in the crawl swimming discipline, wherein one arm is extended above the head and the other arm is extended alongside and behind the body.

The term "butterfly" when used in combination with the indication of the patient's positioning on the breast coach or table refers to the position wherein both arms are elevated above the head, but wherein said arms are slightly flexed. The term resembles the backward arms movement in the butterfly swimming discipline.

Provided herein is a radiotherapy breast board or couch for use in radiotherapy treatment of breast cancer patients. The radiotherapy breast board or couch described herein is particularly suitable for treating the breast and the regional lymph nodes of a patient in prone position. The radiotherapy breast board or couch described herein, also referred herein as "board" or "couch", comprises a caudal part and a cranial part at opposite ends. The caudal part is suitable for attachment to or on a means for supporting the legs and lower part of the trunk of the patient, called a patient support system such as a pedestal, couch table, or robotic arm, whereas the cranial part is provided with a head support. The board or couch can further comprise one, or a pair of opposed, lateral frame member(s) connecting the caudal part and the cranial part. The board or couch further provides an opening allowing for a breast of the patient to pass through as said patient lies in a prone position on said board or couch. This will be explained further herein below.

The patient support system of a radiotherapy table or couch for use with the breast board or couch as described herein typically provides support for the legs and optionally a part of the upper body (trunk) of the patient. The patient support system typically comprises a base or pedestal (2), with a couch table or top (3), for example as shown in FIG. 1 A-C and FIG. 2 A-B. Alternatively, a robotic arm can be used as a patient support system. Modern couch blades or tops often consist of a caudal part which is mounted to the pedestal and a cranial part which extends in air. The cranial part is variably locked to the caudal part by a bipolar connecting system and can be easily removed. Cranial parts of couch blades are available constructed in different shapes adapted to the treatment of different regions of the body: head, neck, thorax, etc. Prone breast boards are placed on top of these caudal and cranial parts. The prone breast couch according to the present invention intends to replaces the cranial part of the couch blade and, in some embodiments, also the caudal part. The breast boards according to the present invention are envisaged to be placed on an existing table blade, e.g. a half blade, thereby creating an opening under the breast and lymph nodes to be treated.

In particular embodiments of the radiotherapy breast couch described herein, the mechanisms between the pedestal and/or robotic arm and the caudal part of the table blade that provide translational and/or rotational movement of the radiotherapy couch are kept in place. This may increase the comfort of the patient and can facilitate irradiation of target regions of the patient's body. Additional pitch and roll capabilities can then be built in the anchorage structure of the breast couch attached to said caudal part of table blade. When using a breast board instead of a breast couch, the breast board can be correctly positioned using additional supporting members of different shapes, thickness, angles and forms, thereby mimicking the pitch and roll positions effected by the anchorage structure of the couch.

In certain embodiments, the prone breast board or couch can be independently moved in one or more directions.

More particularly, it is envisaged that in certain embodiments, the anchorage system to the pedestal of the radiotherapy couch is adapted for changing the pitch and/or roll of the radiotherapy breast couch, i.e. the rotation of the couch along a transverse or cranio-caudal axis of the couch, more particularly an axis running from the patient's left side to the right side or from the feet to the head, when the patient is lying on the couch.

In particular embodiments, the pitch of the prone couch can be changed over an angle of at least 60°, for example from a substantially horizontal position to an elevated, i.e. (almost) vertical position. This can facilitate positioning of the patient on the couch. For example, the couch may first be moved to an elevated position for allowing the patient to take place on the couch e.g. on the knees, followed by moving the couch to a more horizontal position for the actual radiotherapy. In further embodiments, the pitch can be changed over an angle of at least 65°, at least 70°, at least 75°, at least 80°, or at least 85°.

In particular embodiments, the anchorage system may be adapted for changing the roll of the radiotherapy breast couch, i.e. the rotation of the couch along an axis in the caudal-cranial direction. Preferably, the radiotherapy breast couch is able to roll along the longitudinal axis of the patient's body, when the patient is lying on the board or couch. In particular embodiments, the roll of the radiotherapy breast board or couch can be changed over an angle of at least 10°, preferably at least 15°, typically up to 25 or 35°. The possibility to change the roll of the board or couch may allow for an improved positioning of the patient, without requiring changing the patient's position relative to the couch.

In particular embodiments, the rotational and/or translational movement of the radiotherapy breast board, pedestal and/or couch may be achieved by manual movement. Additionally or alternatively, the board and/or couch may be provided with means for controlling its rotational and/or translational movement. Such means may include, but are not limited to (electro)motors, pneumatic actuators, and the like. This may allow for an automated control of the position of the breast board or couch. The control of the motors and/or actuators may be based on feedback from one or more means for monitoring the position of the breast board, pedestal, or couch, such as accelerometers and/or tilt sensors. Accordingly, in certain embodiments, the radiotherapy breast board or couch may be provided with one or more tilt sensors and/or accelerometers.

The radiotherapy breast board or couch described herein is further provided with a cranial part (5) comprising a head support (6) for supporting and immobilizing the patient's head. The head support may be shaped as to surround the patient's face. More particularly, the head support may be provided with a central opening which allows the patient to see and to breathe freely during the therapy. In certain embodiments, the head support may have a horseshoe or annular shape. The head support may comprise a face cushion for increasing the patient's comfort. In certain embodiments, the head support may have a face cushion for increasing hyperextension of the head to increase the distance of the chin away from the irradiation beam.

The head support is preferably made as compact as possible as to increase the mobility of the couch. In particular embodiments, the width of the head support is less than 50% of the width of the (couch top of the) caudal part.

Figure 3:
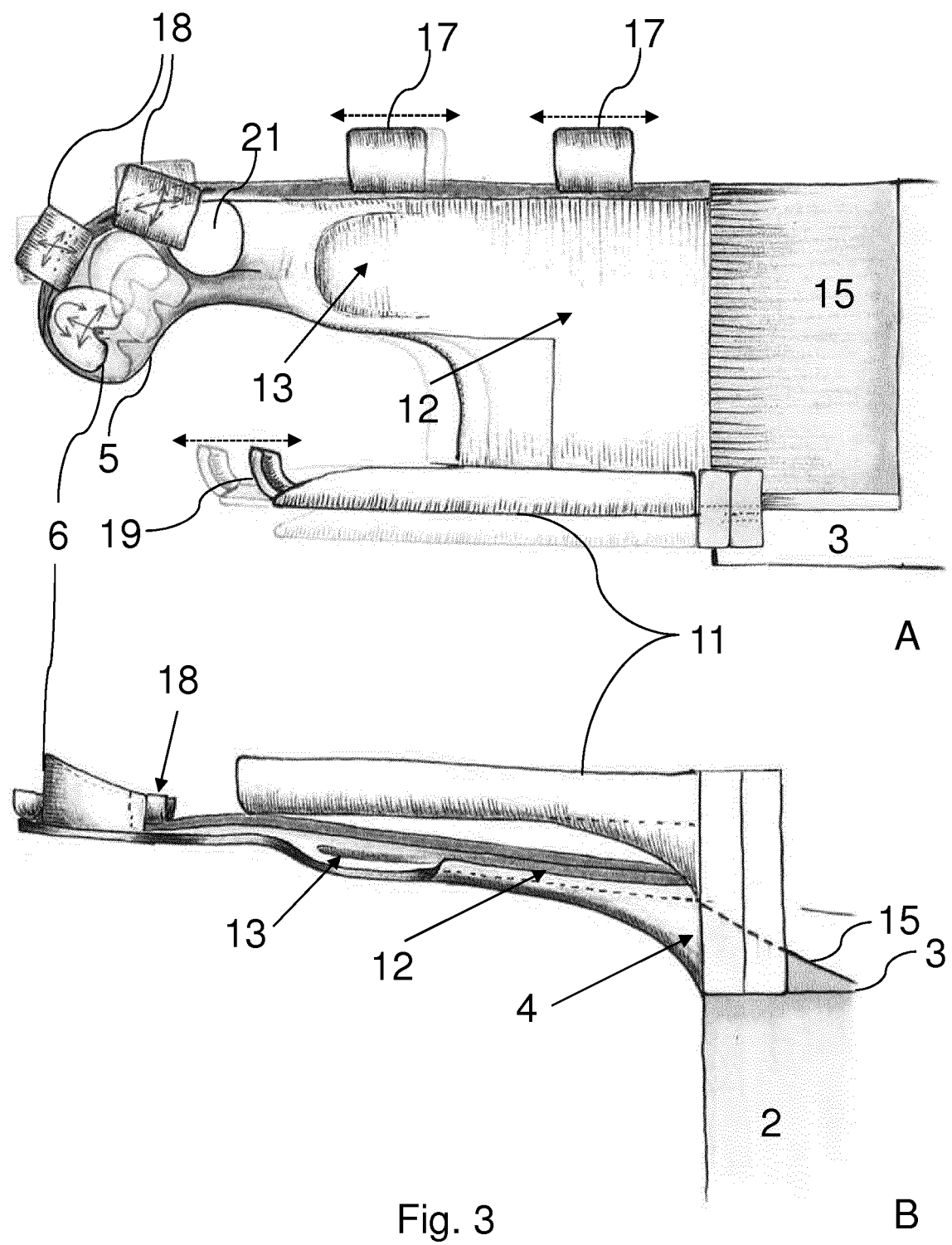
FIG. 3: Schematic view of one embodiment of a left self-supporting breast couch as described herein. A) Top view and B) Side view of the breast couch, comprising a longitudinal body supporting member (12, 13), configured for supporting the non-treated side of the patient's body, including the contralateral breast using a wedge (13), further comprising an anchorage structure (4) for connecting the body supporting member (12) to a radiotherapy couch blade (3) or pedestal (2), and a head support (5, 6), configured to support the head of the patient. The breast couch additionally can comprise a slope (15) to improve the position of the patient, and a longitudinal first arm supporting member (11), configured for supporting the arm of said patient at the side of treatment when held backwards alongside the body, and optionally one or more second arm supporting member(s) (17, 18) attached to the body supporting member (12, 13) or head support (5, 6), configured to support the arm of the patient at the non-treated side. The arm supporting member can also comprise a shoulder supporting member (19), configured to support at least part of the shoulder. As can be seen from the figure, the breast couch creates an open space between the body supporting member (12) and the arm supporting member (11), increasing accessibility of the breast and regional lymph nodes to be treated.

In particular embodiments, the (translational, vertical, and/or rotational) position of the head support may be adjustable. For example, it may be possible to change the distance between the head support and the caudal part of the breast board or couch, e.g. in function of the patient's height. It may further be possible to change the lateral position of the head support, for example depending on which side of the patient needs to be treated. In certain embodiments, the head support may be adapted for rotation along one or more axes of rotation. For example, the head support may be rotatable around a rotational axis in the caudal-cranial direction, thereby allowing for a roll movement of the head support. This can further increase the patient's comfort. The head support may advantageously also be rotationable around its centre as shown in FIG. 3A (cf. Different arrows in head support (6)).

Figure 1B:
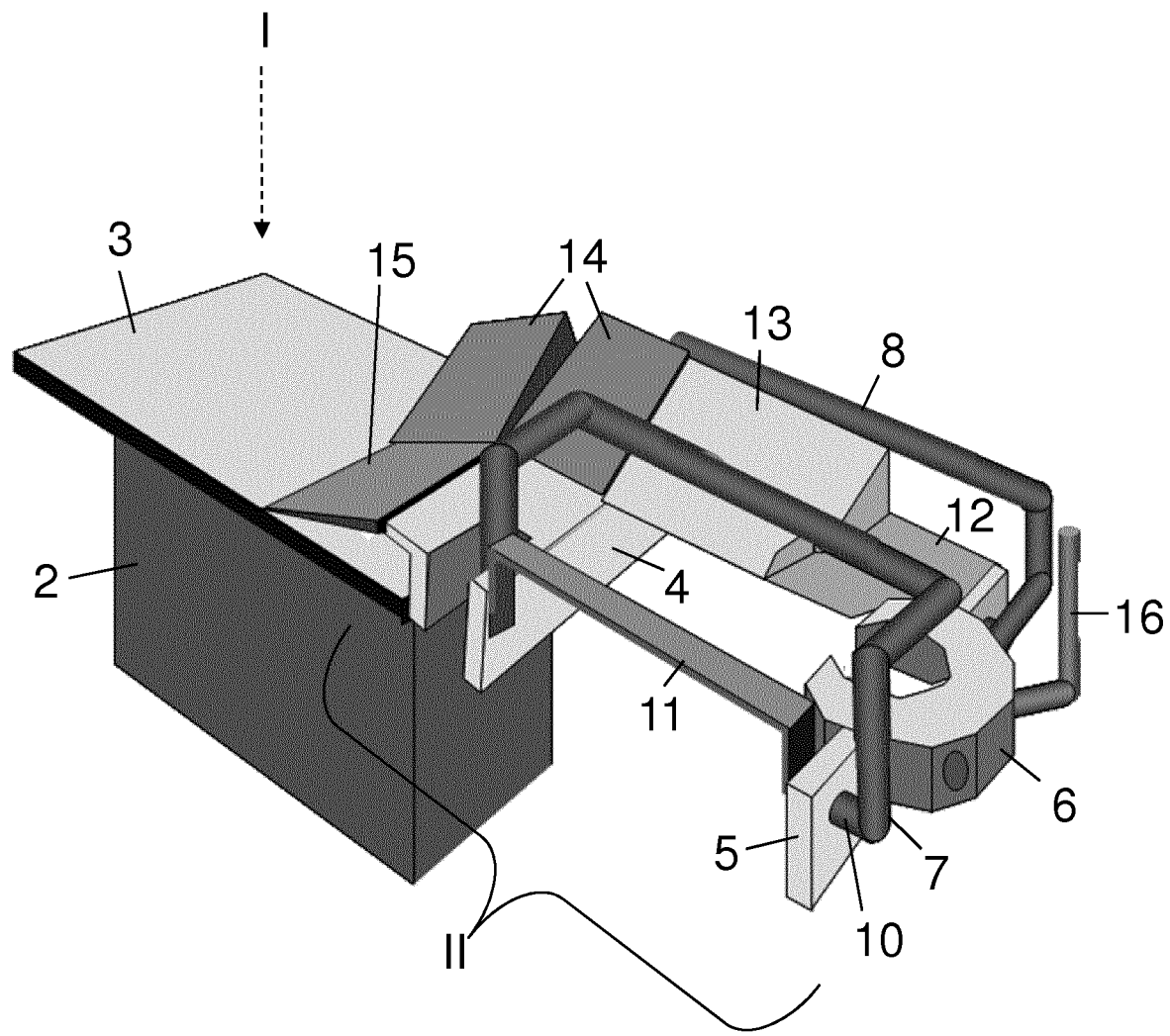
Figure 1C:
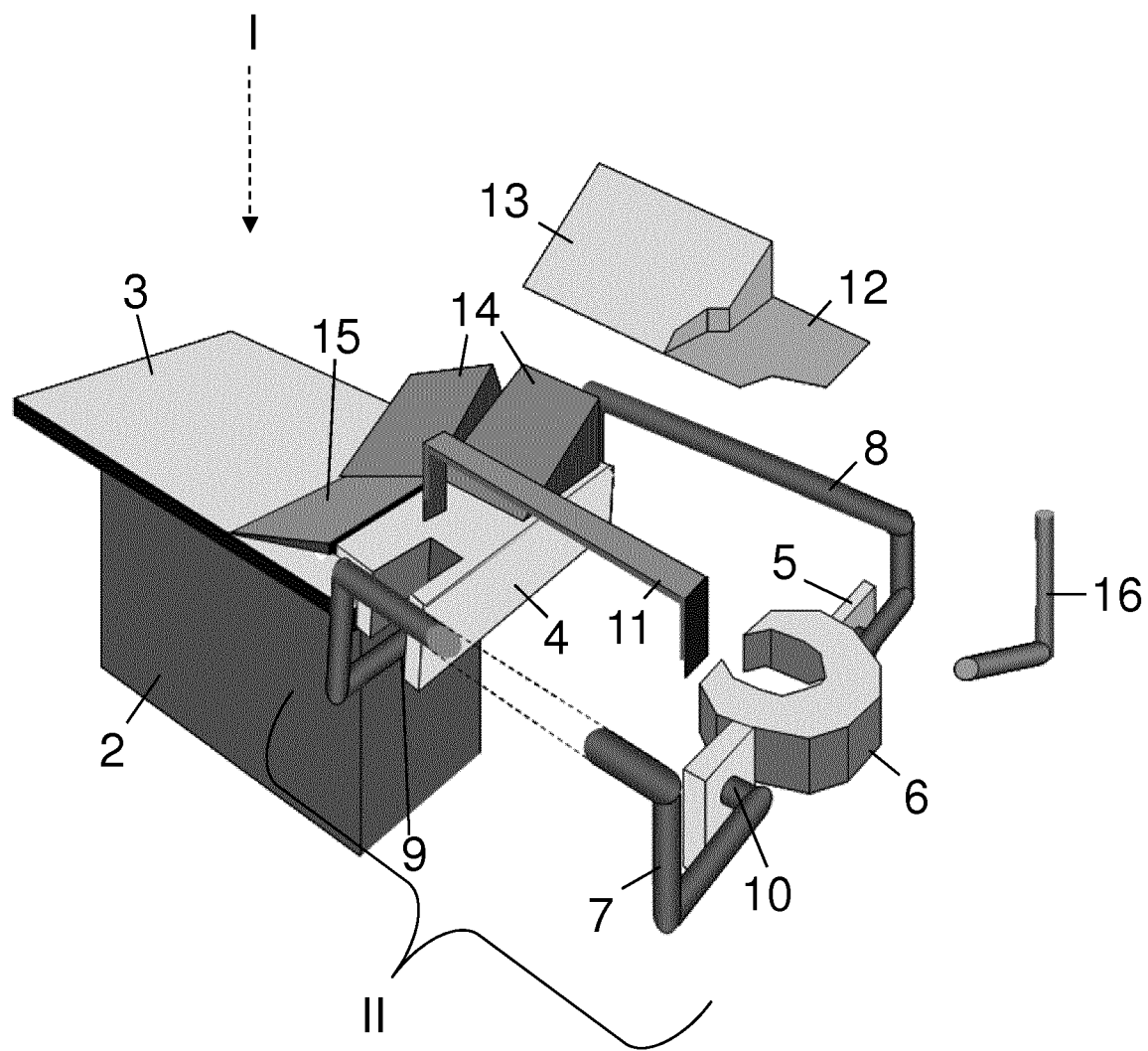
Figure 2A:
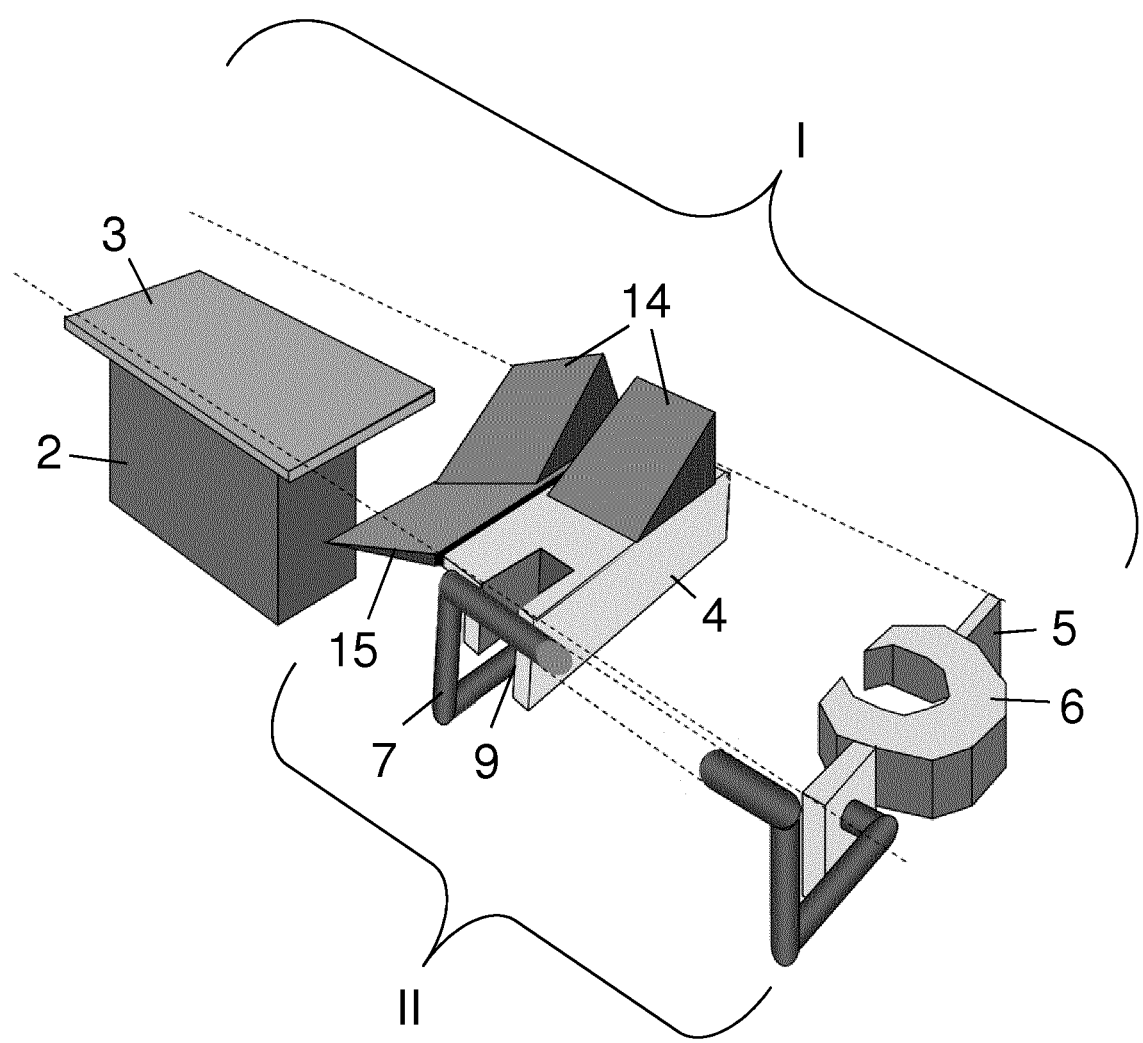
FIG. 2: Exploded view of certain elements of a particular embodiment of the radiotherapy table (I) and supported breast couch (II) described herein. A) symmetric design of a supported radiotherapy couch; B) asymmetric design of a supported radiotherapy couch with a unilateral supporting frame (8) at one side, and an arm support (11) at the other side.
Figure 2B:
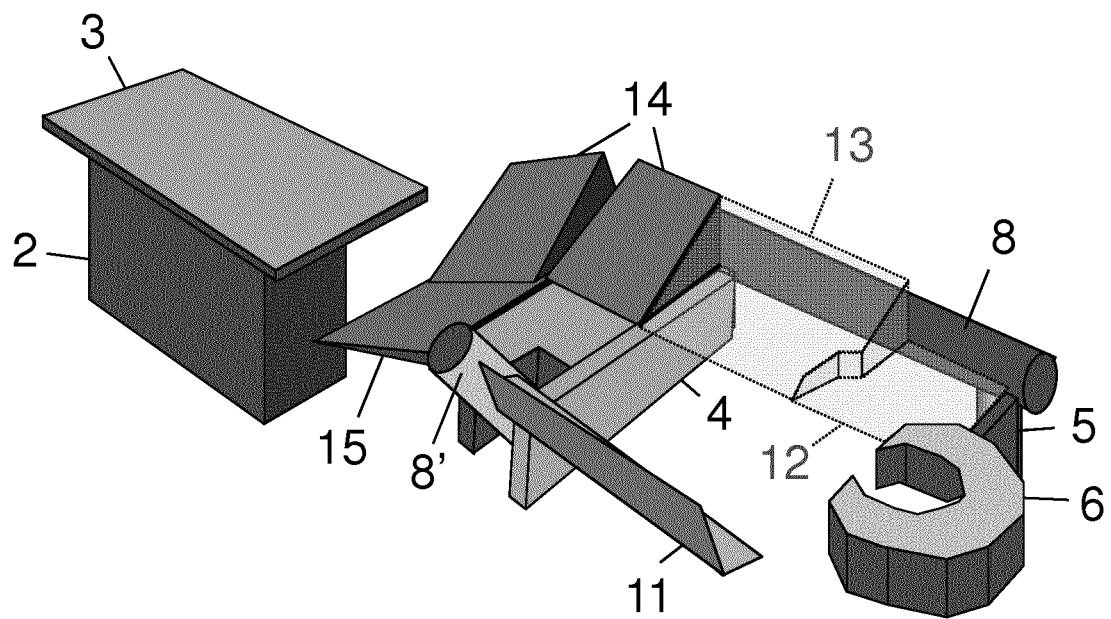
Figure 10A:
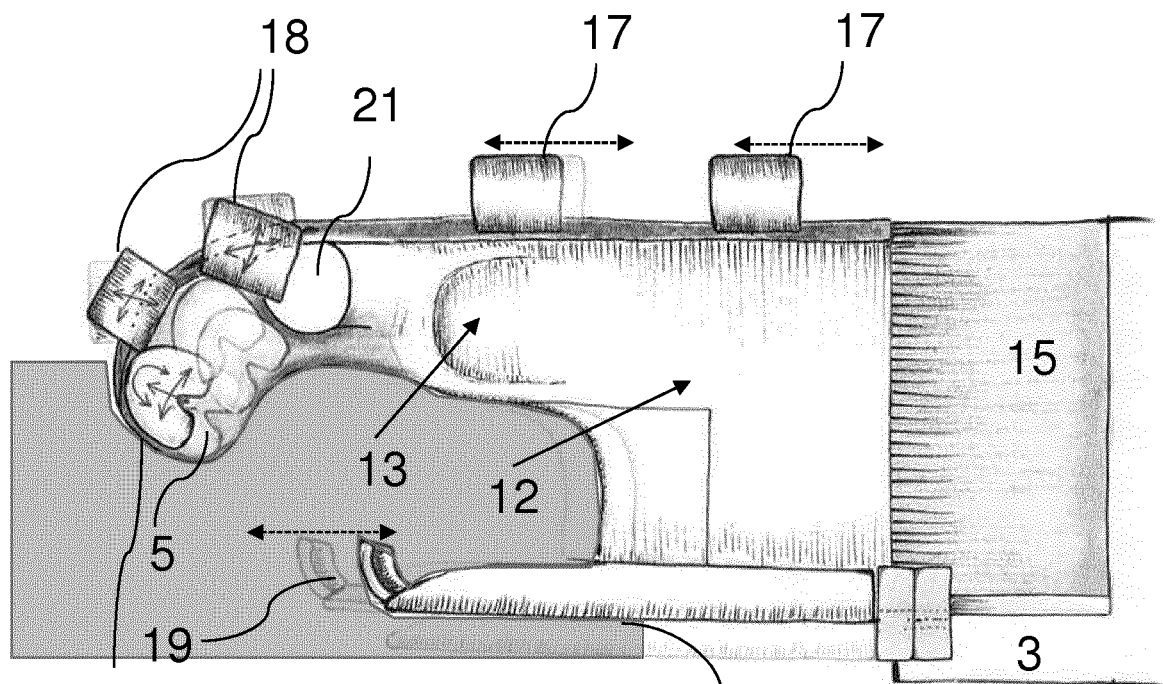
FIG. 10A is a top view of the presently disclosed breast board or couch.
Figure 10B:
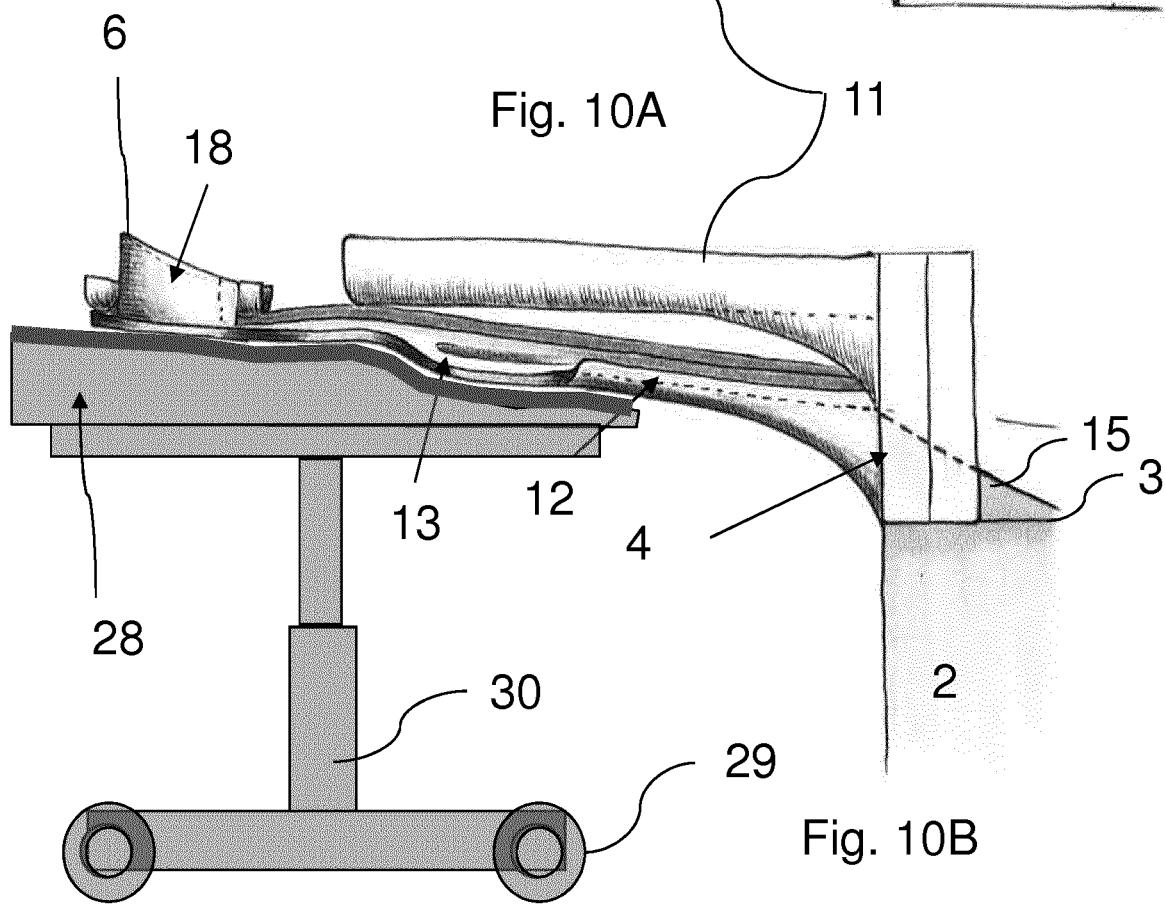
FIG. 10B is a side view of the same. These figures show an embodiment of the removable device (28), in this case presented on a floor-positioned trolley (29) with hydraulic arm (30), which can be positioned under the breast couch, in order to ensure safe positioning of the subject. When positioned under the breast couch, its upper surface closes the large aperture of the breast couch. Hence, the patient will not see the floor underneath when moving towards the prone position on the breast couch. In addition, the patient can lean on the device while moving towards the desired position. Once the patient is correctly positioned and secured, the removable device can be removed, creating the necessary open space for radiation therapy. The removable device (28) has, is in this case, a shaped upper surface structure fitting under the breast board. The shape of the upper surface can be constructed as a docking element that matches the bottom-side of the couch.

The caudal and cranial parts of the radiotherapy breast board or couch can be connected to each other via one or more lateral frame members (7, 8), for example as shown in FIGS. 1 and 2. In FIGS. 1A, 10 and 2A, the first frame member (7) is not shown completely as not to obscure the other features of the breast board or couch. In these figures, the actual shape of the first frame member (7) is indicated by dotted lines. In FIG. 1B, the first frame member (7) is shown in full. In FIG. 2B a design using a single frame member is shown.

The one or more frame members (7, 8) of the radiotherapy breast board or couch described herein ensure the structural integrity of the radiotherapy breast board or couch and are arranged such that they can provide an opening between the frame members, which allows for a breast of the patient to pass through as the patient lies in a prone position on the breast board or couch.

Moreover, each of the frame members can be provided as a straight, angled or bent (continuous) longitudinal bar, for example having a C-shape, preferably connected to the caudal part of the breast board or couch at a first end and to the cranial part at a second end.

Furthermore, the connections between the frame members and the caudal and cranial part can be executed as pivotable connections, which allow for rotation of the frame members (7, 8), more particularly along an axis of rotation in the caudal-cranial direction. Although the axis of rotation need not be the same for both frame members (if present), the axes preferably are parallel. In preferred embodiments, the connection between the frame members and the caudal and cranial part are provided via a pivot bearing (9, 10).

The combination of the pivotable connection and the bent or angled shape of the frame members allows for the frame members to independently travel laterally and/or dorsally along the patient's shoulders. This is illustrated in FIGS. 1A and 1B, which shows a particular embodiment of the radiotherapy couch or breast board described herein, with the first frame member (7) in a lateral position (FIG. 1A) and in a dorsal position (FIG. 1B). By moving the frame members, disturbance of the radiation beam by the frame members can be avoided regardless of the beam position and orientation. In this way, it is possible to treat the patient's breast as well as the regional lymph nodes, using a variety of beam directions without changing the patient's position on the breast board or couch.

The frame members are typically the only support which is provided for the cranial part. Accordingly, the cranial part is typically suspended from the caudal part via the one or more frame members. This results in a light structure which facilitates the positioning of a radiation source (e.g. gantry) anywhere around the patient's torso.

The frame members are typically made of metal, e.g. (stainless) steel, aluminium, titanium or alloys thereof, or the like. Alternatively, composite or fibre enforced polymeric, foam, or plastic materials can be used. These materials allow for the manufacture of frame members provide an adequate strength and durability with a minimal width of the bar. However, it is not excluded that the frame members may be made of other materials. The bar(s) comprised by the frame members may be solid or hollowed.

In particular embodiments, the radiotherapy breast board or couch may be provided with further means for supporting and/or immobilizing the patient's body, such as additional arm supports (16, 17, 18, 11'), support cushions (14), and the like. Preferably, these means are removably connected or connectable to the breast board or couch, and/or may be movable relative to the radiotherapy breast board or couch. In this way, the breast board or couch can be adapted to the patient's needs for providing an optimal comfort.

In preferred embodiments, the radiotherapy breast board or couch is provided with a first arm support (11) positioned parallel to or between the (two) frame member(s), and connected to the caudal part and optionally the cranial part of the breast board or couch, for supporting a first arm of said patient positioned alongside the patient's body. The first arm support is positioned such that the radiotherapy breast board or couch still provides an opening allowing for a breast of the patient to pass through as the patient lies in a prone position on the breast board or couch.

The first arm support (11) typically has a longitudinal through of half-tube-like shape and provides a support surface having a longitudinal shape. The width of the support surface amounts to between 5 and 15 cm, preferably between 8 and 10 cm. In particular embodiments, a mould made of the shape of the individual patients arm can be connected on the support surface with press studs.

This can provide an adequate support area for the patient's arm, while causing no or only minimal beam interference.

With the proposed radiotherapy breast board or couch, the patient is typically positioned with the arm at the patient's side to be treated alongside the body. This significantly increases the radiation beam access range to the regional lymph nodes, compared to a situation wherein the patient's arm is raised. Accordingly, the proposed couch or board can allow for treating the breast as well as the regional lymph nodes, in a single patient setup and in a single radiation treatment step.

The nature of the connection of the first arm support to the remainder of the radiotherapy breast board or couch is not critical. In particular embodiments, as shown in FIG. 2B, the connection of the first arm support to the caudal part may allow for (lateral, longitudinal and vertical) movement of the first arm supporting member (11) relative to the remainder of the breast board or couch, more particularly relative to the caudal part and cranial part. This may allow for adapting the position of the arm support in function of which organs or tissues of the patient require treatment, and/or to the patient's anatomy. For example, the caudal and cranial part may be provided with a slide bearing or rail system for allowing lateral movement of the first arm support. Additionally or alternatively, the first arm support may be removable.

In such embodiments, a number of different arm supports may be provided, each adapted for a radiotherapy target and/or different anatomy.

In certain embodiments, the radiotherapy breast board or couch described herein may be provided with one or more second arm support(s) (16, 17, 18, and/or 11'), for supporting the other arm of the patient, more particularly the arm at the non-treated side (contralaterally) of the patient.

With the present radiotherapy board or couch, the patient is typically positioned with the arm on the non-treated side raised above the head. The breast board or couch may further be provided with a dedicated handle (16) for supporting the patient in this position. Alternatively, the patient may hold both arms alongside the body during the radiotherapy.

Similar to the first arm support (11) described above, the one or more second arm supporting members (17, 18, and/or 11') are positioned between the two frame members, and connected to the caudal part (5) and/or the body supporting member (12). The second arm support typically provides a support surface having a longitudinal shape, such as a through or a half-pipe. The surface area of the support surface of the second arm support can be wider than the surface area of the support surface of the first arm support.

The second arm supporting member(s) can be provided with additional support elements (see further) which can further support and/or immobilize the patient's body. Exemplary positions of the supporting members (11', 17 and 18) are shown in the figures.

Also similar to the first arm support, the position of the second arm support (17) may be adjustable, e.g. via a rail mechanism; and/or the second arm support may be removable. If the first and second arm support both are removable, this can allow for reversing the position of the first and second arm support, depending on which side of the patient needs to be treated.

If present, the first and second arm supports are positioned such that an opening is provided between the arm supports, allowing for a breast of the patient to pass through as the patient lies in a prone position on the couch. Typically, the opening will have a longitudinal shape, thereby providing undisturbed access to the breast to be treated as well as the regional lymph nodes.

In particular embodiments, the radiotherapy breast board or couch may be provided with a number of support elements and/or support cushions (14). The support elements and/or support cushions may be provided on various parts of the radiotherapy couch (or breast board), as shown in FIG. 1.

In particular embodiments, the breast board or couch may be provided with a wedge support (13), i.e. a wedge-shaped support element. The wedge support (13) can be positioned on the body supporting member (12) for supporting the patient's contralateral shoulder and/or torso on the non-treated side and enabling the contralateral breast to be positioned outside the radiation field. The wedge support (13) on the body supporting member (12) typically is positioned with the wide edge pointing away from the patient.

In particular embodiments, the wedge support may be transparent, translucent, or radiolucent. It can e.g. be made up out of polycarbonate or PETG. This may facilitate monitoring whether the radiation beam hits the non-treated breast or other body parts which are not to be irradiated. The radiation beam is monitored in such a way that the beam does not pass through the non-irradiated (contralateral) breast but in particular embodiments the beam may hit the non-treated breast due to movements of the patient laying on the breast board or couch. This optical control in such circumstances allows repositioning before starting the treatment.

The design of the wedge shows at the medial side an upwards curvature which differs from the existing typical flat surface wedges. This curvature projects the non-treated (contralateral) breast further away from the radiation beam and avoids adverse effects of shadow projection typically for flat surfaces during CT-imaging. Shadow effects can seriously disturb the CT-image quality and complicate the definition of regions of interest.

In certain embodiments, the breast board or couch may be provided with a number of support cushions (14) for providing additional support and comfort to the patient.

In certain embodiments, the radiotherapy couch or board may be provided with a slope element (15) for bridging any height difference between a pedestal (2) or couch top (3) and a couch extension (see further). The slope element typically is wedge-shaped and may have a soft or hard surface.

In other embodiments, said cushions (14), slope (15), and wedge (13), can be part of a single structure, e.g. a foam-based structure, adapted to the anatomy of the patient population or specific patient.

In the radiotherapy breast couch as described herein, the frame members may be connected directly to the patient support system (e.g. pedestal, or robotic arm) and/or couch top or blade of the caudal part. However, in other embodiments, the frame members may be connected to the caudal part via an intermediary structure. More particularly, the frame members (and consequently the cranial part) may be provided on an anchorage structure (4), which can be mounted and locked onto a pedestal or base. Thus, the radiotherapy couch as described herein may be designed as a full length couch or can be functioning as a couch extension to be fitted to an existing patient support system. FIG. 2 shows a particular embodiment of such breast board functioning as a couch extension, separate from the pedestal (2) and couch top (3).

The anchorage structure of the breast board may be mounted onto the patient support system, pedestal, caudal couch blade or robotic arm of the different available radiotherapy tables or patient support systems. Depending on the type of table, the anchorage structure can be clipped in the table or couch, or can be anchored to the couch or table using the known connectors such as straight or hook shaped metal connectors.

As described above, the caudal part of the radiotherapy table, or its table blade will typically be adapted to provide translational (lateral, longitudinal and/or vertical) and/or rotational (pitch and roll) movement of the radiotherapy table blade. Additionally or alternatively, the anchorage structure and/or the coupling between the caudal part and the anchorage structure may be adapted to provide said, or additional, translational and/or rotational movement of the anchorage structure relative to the caudal part.

In certain embodiments, the (coupling between the caudal part and the) anchorage structure may be adapted to provide rotational movement of the anchorage structure (and thus also of the cranial part and frame members) relative to the caudal part, along one or more axes of rotation.

More particularly, it is envisaged that in certain embodiments, the (coupling between the caudal part and the) anchorage structure is adapted for changing the pitch of the cranial part and frame members relative to the caudal part, i.e. a rotation along a transverse axis of the couch. In particular embodiments, the anchorage structure allows for rotation of the cranial part relative to the caudal part over an angle of at least 10°, preferably at least 15°.

In particular embodiments, the (coupling between the caudal part and the) anchorage structure may be adapted for changing the roll of the cranial part and frame members relative to the caudal part. In particular embodiments, the roll of the frame members and cranial part relative to the caudal part can be changed over an angle of at least 10°, preferably at least 15°.

As described above, the rotational and/or translational movement may be achieved manually and/or via other means such as actuators.

Further provided herein is a method of performing radiotherapy treatment, involving the use of a radiotherapy couch or board as described herein. The method comprises the steps of:

(a) positioning the patient in prone position on a radiotherapy prone breast couch or board as described herein, wherein the breast to be treated is allowed to hang from an opening provided therefore;
(b) verifying and eventually adapting the patient position
(c) irradiating the breast to be treated;
(d) optionally, simultaneously irradiating the regional lymph nodes surrounding the breast to be treated.

In a preferred embodiment, the method comprises the steps of:
(a) positioning the patient in prone position on a radiotherapy prone breast board positioned on an imaging table, wherein the breast to be treated is allowed to hang from an opening provided therefore;
(b) verifying and eventually adapting the patient position though imaging techniques such as CT scan;
(c) replicating the position of the patient in step b) on a radiotherapy breast couch as described herein,
(d) irradiating the breast to be treated;
(e) optionally, simultaneously irradiating the regional lymph nodes surrounding the breast to be treated.

In preferred embodiments, step (a) involves positioning the patient with the arm on the side of the breast to be treated alongside the patient's body. This facilitates access to the regional lymph nodes. This also reduces folds in the skin of the patient increasing radiation efficiency and reducing radiation toxicity in the skin and surrounding tissue.

In other embodiments, the other arm may be raised above the patient's head.

Optionally, said positioning may involve changing the position of one or more of the frame members (7, 8) or supporting members (11, 11', 12, 17, and/or 18). More particularly, one or both frame members may be pivoted to prevent the frame members from disturbing the irradiation beam.

In a particular embodiment (cf. FIG. 1), the invention hence provides a the radiotherapy table (I) to which a symmetrical C-arm supported breast couch (II) is attached as described in one of the embodiments herein. The radiotherapy table (I) comprises a base or pedestal (2) with the caudal part of a couch blade (3). The couch blade (3) provides connector devices for the anchorage structure (4) of the breast couch (II). The anchorage structure is connected to a cranial structure (5) having a head support (6) via one or more frame members, in this exemplary case C-arms (7, 8). Said one or more frame members (7, 8) are each connected to the anchorage structure (4) and the cranial structure (5) or head support via e.g. pivot bearings (9, 10). The radiotherapy couch can further comprise elements for supporting the patient, including an arm support (11), a body supporting member (12, 13), cushions (14), a slope element (15), and a further arm supporting member or handle (16).

In further particular embodiments (cf. FIG. 2) of the radiotherapy table (I) and supported breast couch (II) described herein. A) symmetric design of a supported radiotherapy couch; B) asymmetric design of a supported radiotherapy couch with a unilateral supporting frame (8) at one side, and an arm support (11) at the other side.

In another embodiment, the invention provides for a left (FIG. 3) or right self-supporting breast couch comprising a longitudinal body supporting member (12, 13), configured for supporting the non-treated side of the patient's body, including the contralateral breast using a wedge (13), further comprising an anchorage structure (4) for connecting the body supporting member (12) to a radiotherapy couch blade (3) or pedestal (2), and a head support (5, 6), configured to support the head of the patient. The breast couch additionally can comprise a slope (15) to improve the position of the patient, and a longitudinal first arm supporting member (11), configured for supporting the arm of said patient at the side of treatment, and optionally one or more second arm supporting member(s) (17, 18) attached to the body supporting member (12, 13) or head support (5, 6), configured to support the arm of the patient at the non-treated side. The arm supporting member can also comprise a shoulder supporting member (19), configured to support at least part of the shoulder. As can be seen from the figure, the breast couch creates an open space between the body supporting member (12) and the arm supporting member (11), increasing accessibility of the breast and regional lymph nodes to be treated.

Figure 4:
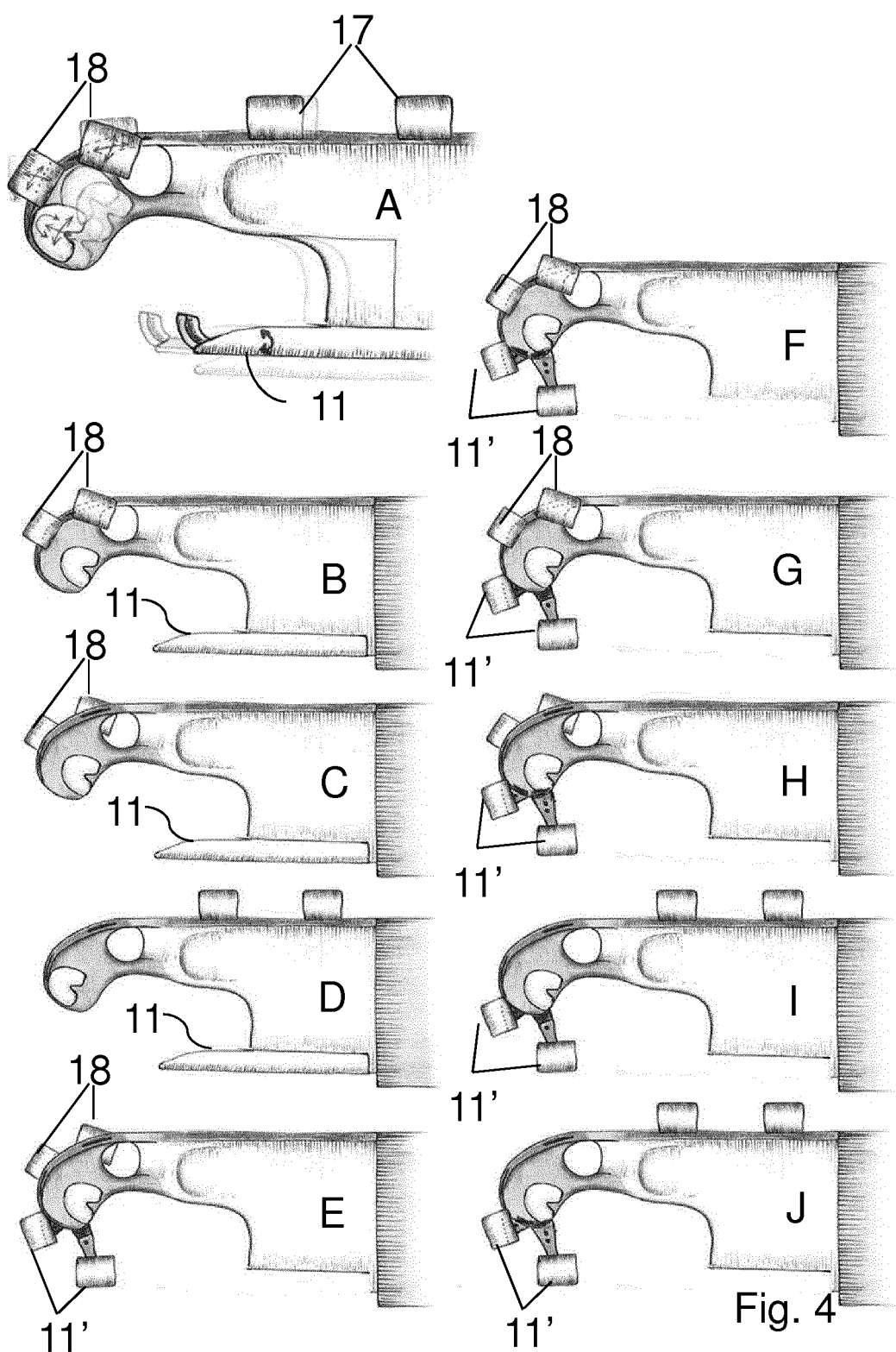
FIG. 4: Shows the possible configurations of additional arm supporting members (17 and 18) connected to the head support (5, 6) and/or body supporting member (12). These additional supporting members allow the patient to position his arms in e.g. crawl, skeleton, or butterfly positions. A): position of first arm supporting member (11) and second arm supporting members (18) allowing the patient to put both arms backwards alongside the body (skeleton), the contralateral arm slightly elevated above the body; B) position of first (ipsilateral) arm supporting member (11) and second arm supporting members (18) allowing the patient to put the first (ipsilateral) arm backwards alongside the body, and the contralateral arm above or behind the head (crawl); C) position of first (ipsilateral) arm supporting member (11) and second arm supporting members (18) allowing the patient to put the first ipsilateral arm backwards alongside the body, and the contralateral arm above or in front of the head. In this case, the contralateral arm goes through the opening (21) and is supported under the breast couch; D) same as A), but with the contralateral arm positioned slightly lower than the body, i.e. the arm goes through the opening (21) and is supported under the breast couch by arm supporting members (17); E) position of arm supporting members (17 and 18) on the head support (5, 6) allowing the patient to put both arms above the head, under the breast couch; F) same as E), but with both arms slight above the breast couch; G) same as E), but with contralateral arm above breast couch and first arm below breast couch; H) same as E), but with contralateral arm under breast couch and first arm above breast couch; I) position wherein the contralateral arm is positioned alongside the body (above or below the breast couch), and the first arm is positioned above the head, under the breast couch; J) same as I, but with first arm positioned above breast couch.

The possible configurations of additional arm supporting members (17 and 18) connected to the head support (5, 6) and/or body supporting members (12) are exemplified in FIG. 4. These additional supporting members allow the patient to position his arms in e.g. crawl or butterfly positions. A): position of first arm supporting member (11) and second arm supporting members (18) allowing the patient to put both arms alongside the body, the contralateral arm slightly elevated above the body; B) position of first arm supporting member (11) and second arm supporting members (18) allowing the patient to put the first arms alongside the body, and the contralateral arm above or behind the head; C) position of first arm supporting member (11) and second arm supporting members (18) allowing the patient to put the first arm alongside the body, and the contralateral arm above or in front of the head. In this case, the contralateral arm goes through the opening (21) and is supported under the breast couch; D) same as A), but with the contralateral arm positioned slightly lower than the body, i.e. the arm goes through the opening (21) and is supported under the breast couch by arm supporting members (17); E) position of arm supporting members (17 and 18) on the head support (5, 6) allowing the patient to put both arms above the head, under the breast couch; F) same as E), but with both arms slight above the breast couch; G) same as E), but with contralateral arm above breast couch and first arm below breast couch; H) same as E), but with contralateral arm under breast couch and first arm above breast couch; I) position wherein the contralateral arm is positioned alongside the body (above or below the breast couch), and the first arm is positioned above the head, under the breast couch; J) same as I, but with first arm positioned above breast couch.

Figure 5A:
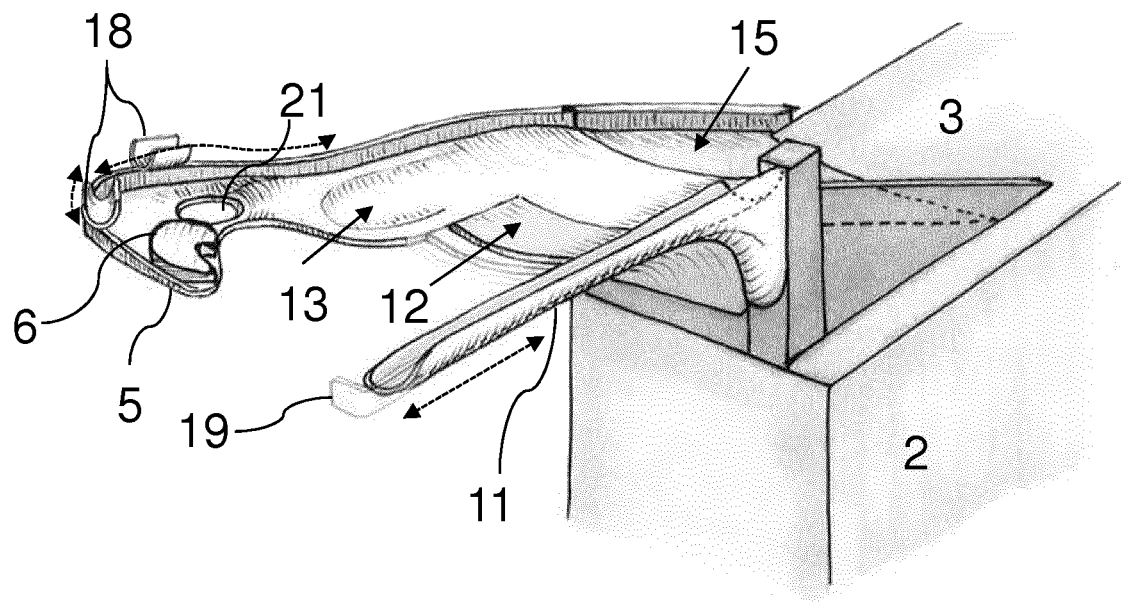
FIG. 5: Schematic view of one embodiment of a left asymmetric self-supporting breast couch as described herein. A) showing the possibility to adjust the length of the first arm supporting member (11) and its optional shoulder supporting member (19). B) shows the vertical adjustment option of the first arm supporting member (11) and its optional shoulder supporting member (19). Note the additional arm supporting members (18), that can be moved alongside the head support (5), or body supporting member (12). Note also the wedge (13) that can be seamlessly incorporated in the body supporting member (12), configured to move the contralateral breast away from the irradiation field.
Figure 5B:
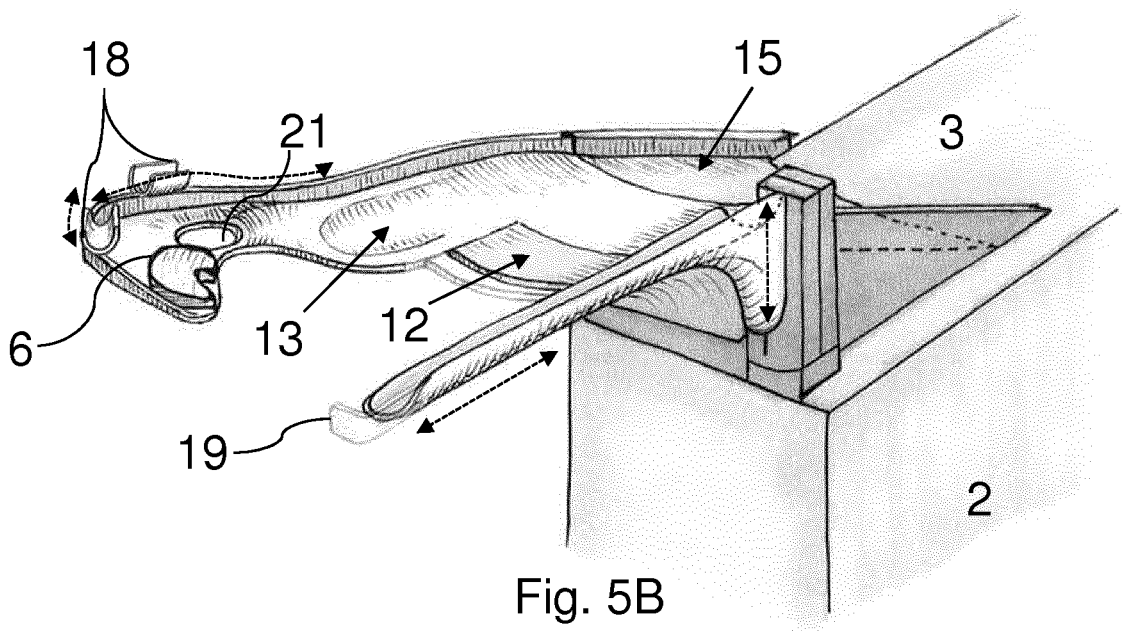

In one embodiment of a left asymmetric self-supporting breast couch as described herein, the possibility exists to adjust the length of the first arm supporting member (11) and its optional shoulder supporting member (19) (cf. FIG. 5A). Also, vertical adjustment of the first arm supporting member (11) and its optional shoulder supporting member (19) is possible (cf. FIG. 5B). Note the additional arm supporting members (18), that can be moved alongside the head support (5), or body supporting member (12, 13). Note also the wedge (13) in the body supporting member, configured to move the contralateral breast away from the irradiation field.

Figure 6A:
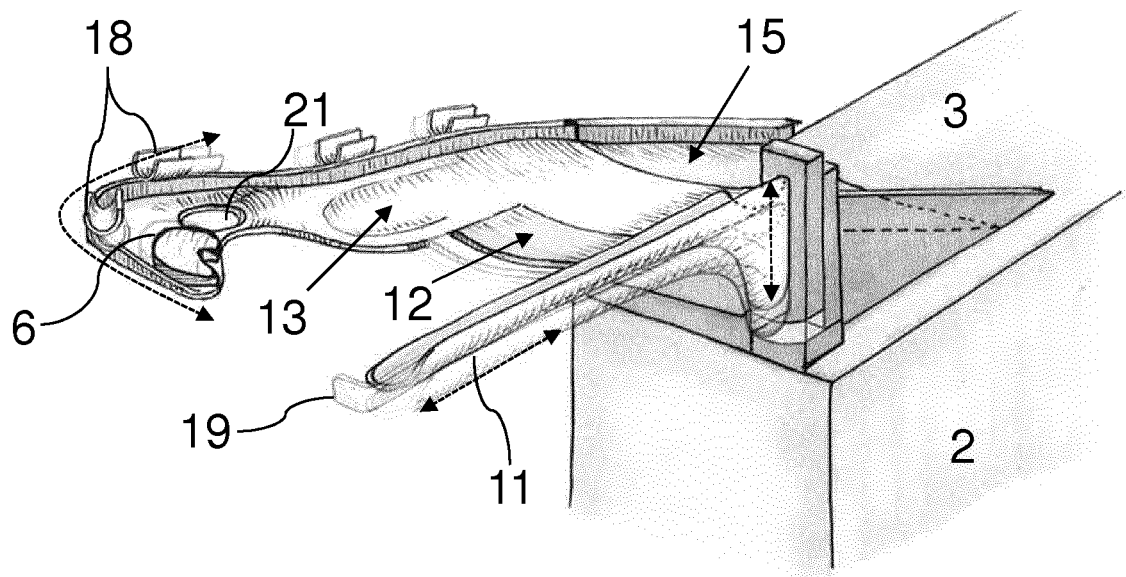
FIG. 6: Shows the adjustability of the arm supporting members A) shows that the first arm supporting member (11) can be adjusted vertically. The arm supporting member is also slightly inclined versus the body supporting member, in that the wrist support lies above upper-arm support; B) shows the adjustability of the first arm supporting member (11), longitudinally, vertically, and axially. By extra rotation of the first arm supporting member (11), the arm and shoulder of the patient can be extended maximally, enabling e.g. better coverage of the lymph nodes. Note the presence of contralateral arm supporting members (18) on the head supporting member and (17) on the body supporting member, that can be moved alongside said supporting members for optimal positioning of the arm.
Figure 6B:
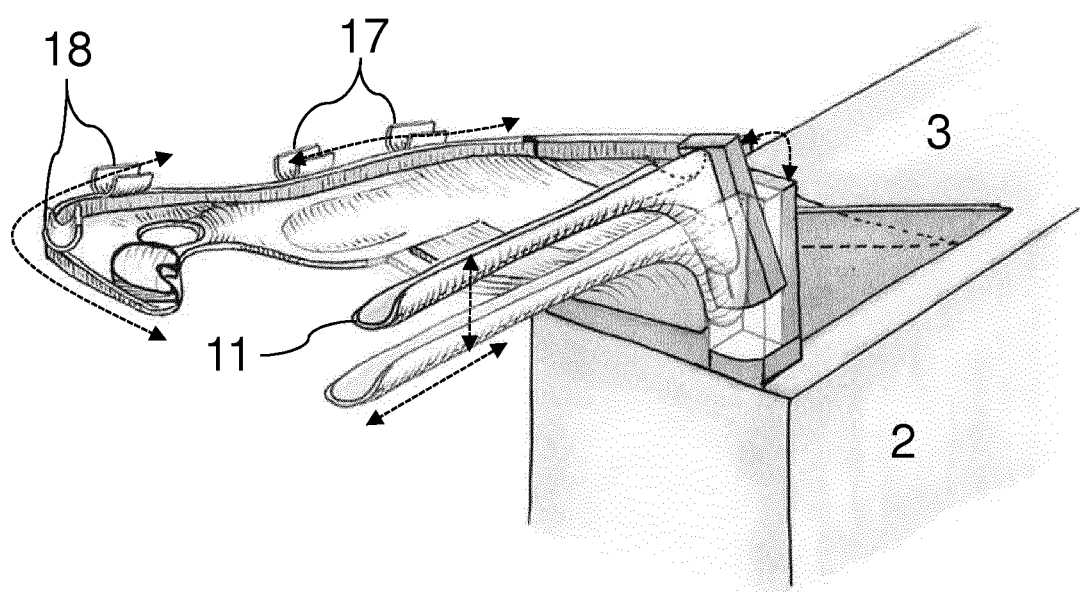

The arm supporting member (11) can be adjusted vertically (cf. FIG. 6A). The arm supporting member is also slightly inclined versus the body supporting member, in that the wrist support lies above upper-arm support; The first arm supporting member (11), is also adjustable longitudinally, vertically, and axially (cf. FIG. 6B). By extra rotation of the first arm supporting member (11), the arm and shoulder of the patient can be extended maximally, enabling e.g. better coverage of the lymph nodes. Note the presence of contralateral arm supporting members (18) on the head supporting member and (17) on the body supporting member, that can be moved alongside said supporting members for optimal positioning of the arm.

Figure 7A:
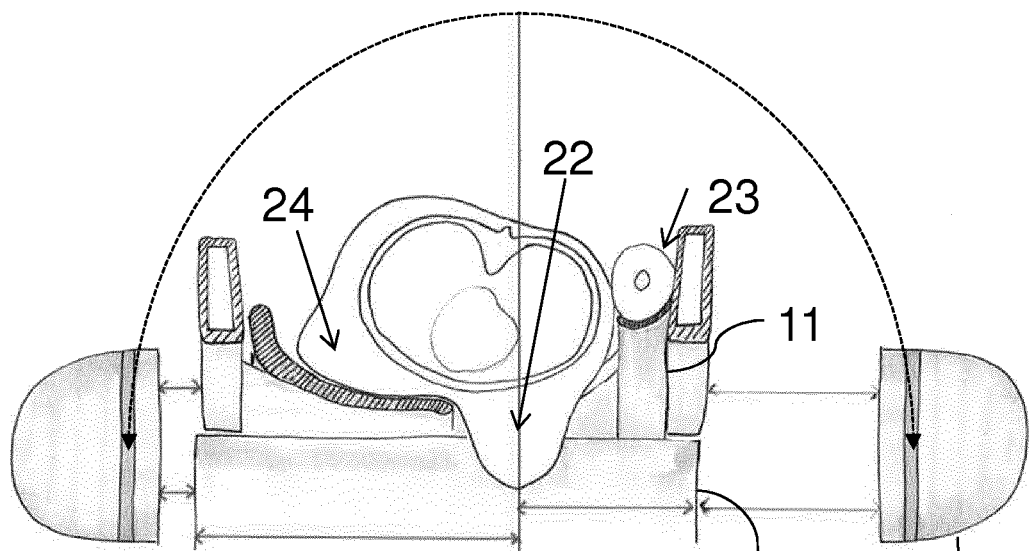
FIG. 7: Shows the advantage of the asymmetric breast couch according to one embodiment of the present invention, over a symmetric embodiment. A symmetrical breast couch (A) has limited maneuverability versus the asymmetric breast couch (B). The asymmetric breast couch allows a lateral shift of the breast couch versus the pedestal (2) in order to aim the isocenter axis (along line 26) of the gantry (25) inside the breast to be treated (22), rather than at the sagittal midplane of the patient. With a symmetric breast couch, the space between the gantry and the breast couch is usually more limited. The figure also shows a transversal view of the patient lying on the breast couch and the effect of the body supporting member (12) and wedge (13) for positioning the contralateral breast away from the radiation beams, as well as the effect of the first arm supporting member (11), for positioning the arm of the patient at the side of treatment away from the irradiation beams.
Figure 7B:
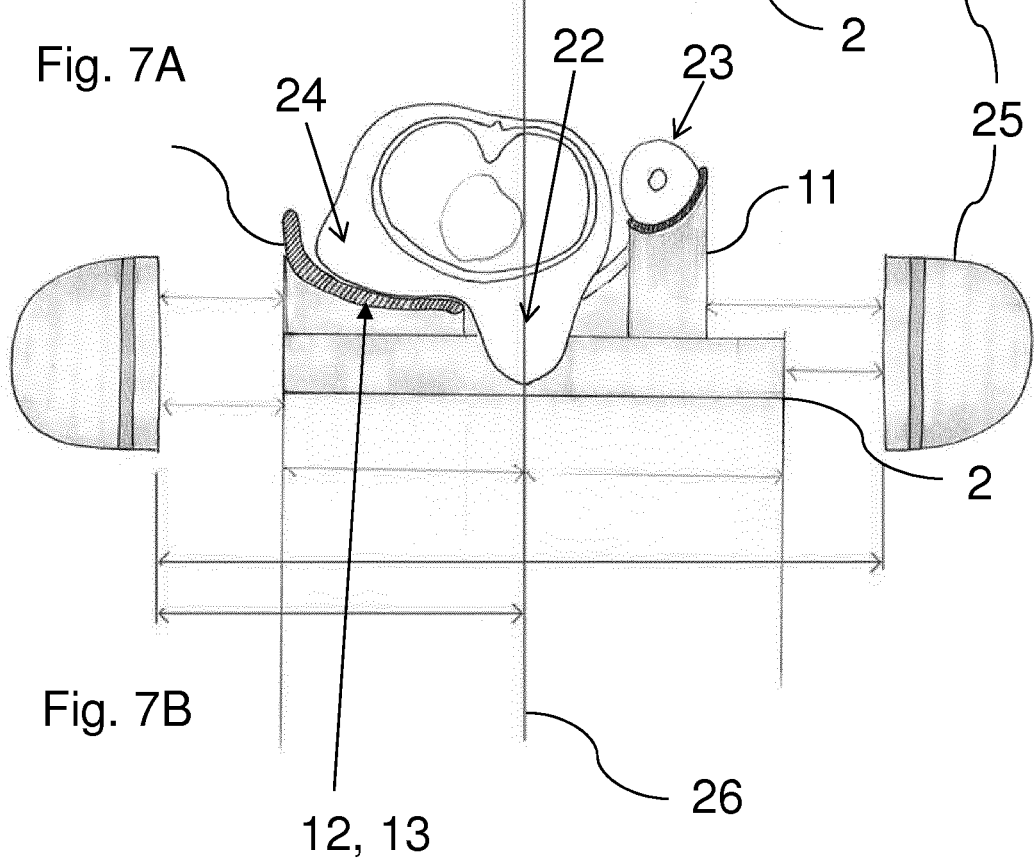

The advantage of the asymmetric breast couch according to one embodiment of the present invention, over a symmetric embodiment are shown in FIG. 7. A symmetrical breast couch (cf. FIG. 7A) has limited maneuverability versus the asymmetric breast couch (cf. FIG. 7B). The asymmetric breast couch allows a lateral shift of the breast couch versus the pedestal (2) in order to aim the isocenter axis (along line 26) of the gantry (25) inside the breast to be treated (22), rather than at the sagittal midplane of the patient. With a symmetric breast couch, the space between the gantry and the breast couch is usually more limited. The figure also shows a transversal view of the patient lying on the breast couch and the effect of the body supporting member (12) and wedge (13) for positioning the contralateral breast (24) away from the radiation beams, as well as the effect of the first arm supporting member (11), for positioning the arm of the patient at the side of treatment away from the irradiation beams.

Figure 8:
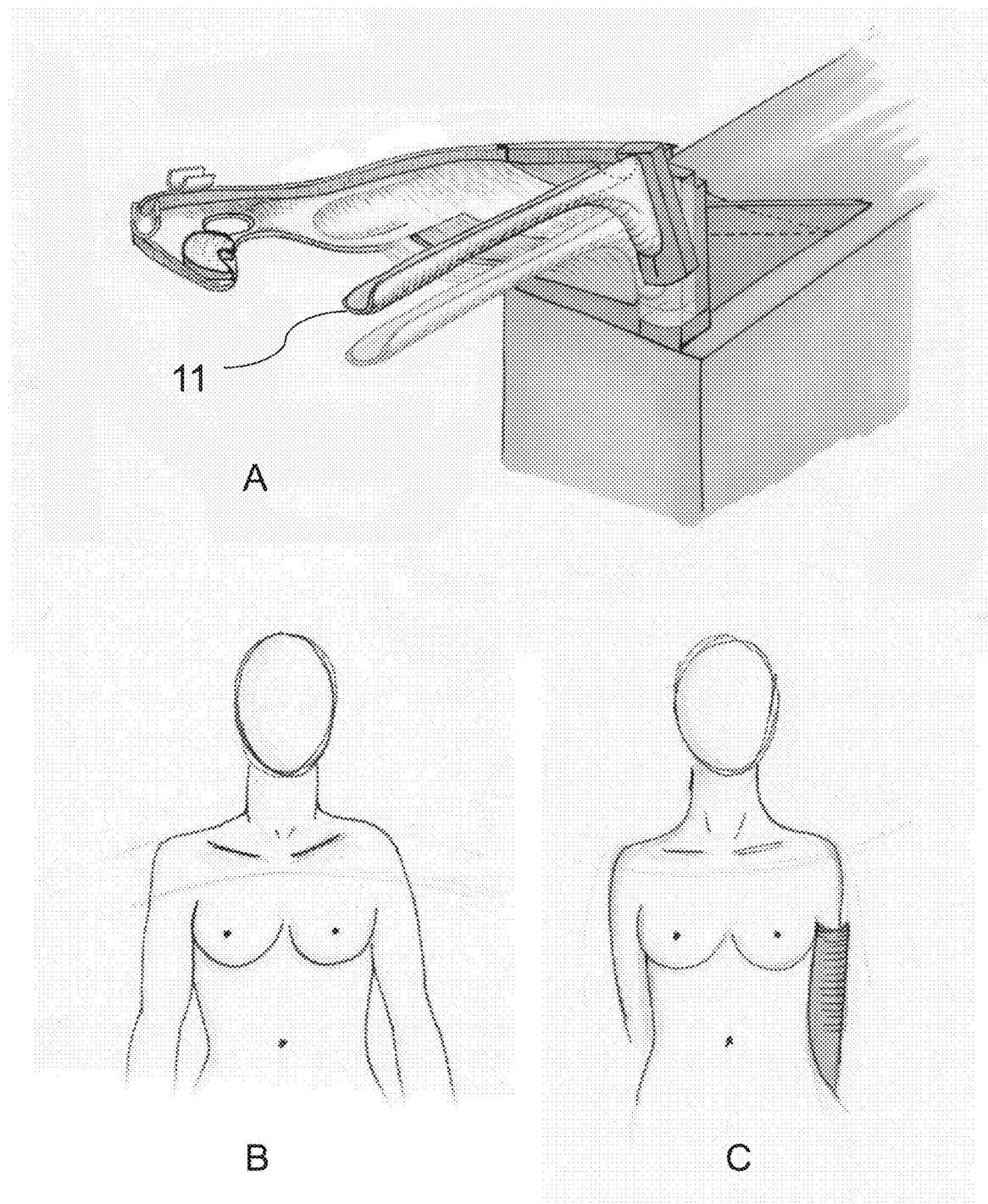
FIG. 8: Shows the effect of rotating and/or tilting the first arm support (11) on the position of the shoulder of the patient to be treated.

The effect of rotating or tilting the first arm support (11) on the position of the shoulder of the patient to be treated is shown in FIG. 8. In panel B versus C, the shoulder of the patient is moved backwards due to the positioning of the arm supporting member (11), which results in optimal stretching of the skin, and optimal positioning of the breast and lymph nodes to be treated.

Figure 9:
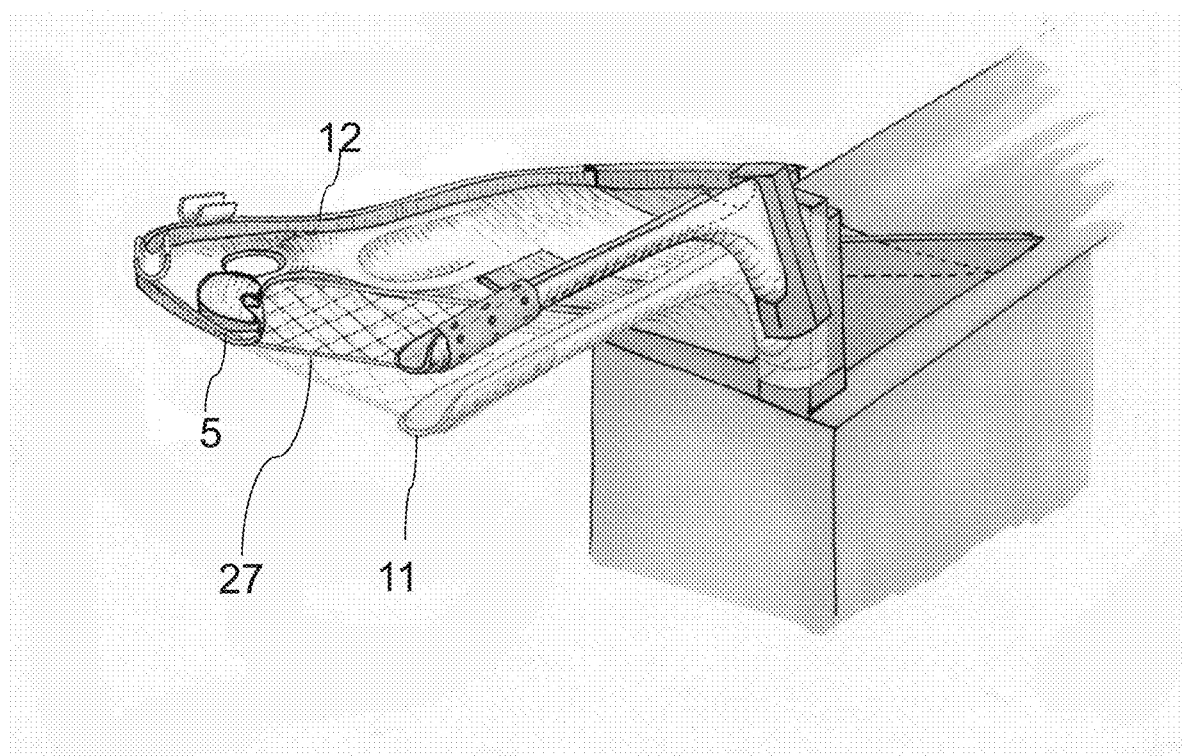
FIG. 9: Shows an optional mesh or net (27) hanging between the body supporting member (12), or cranial structure (5), enabling safe positioning of the patient on the breast couch. The mesh or net can also be used during the irradiation by patients who do not have enough muscle tonus to hold the optimal position during the radiotherapy process and to achieve hypoxia of the skin.

In some embodiments, an optional mesh or net (27) hanging between the body supporting member (12), or cranial structure (5) can be present enabling safe positioning of the patient on the breast couch (FIG. 9). Such a mesh or net can be in thermoplastic material, or nylon, or any other type of suitable supporting net structure or mesh. It can furthermore facilitate and secure the positioning of patients with insufficient muscle tonus. A typical radiation therapy encompasses daily radiations (e.g. 5 times per week for 3 to 5 weeks), which may result in light burns of the skin. Applying a mesh or net will reduce this, since the pressure of the net or mesh applied on the skin will result in local hypoxia, which will reduce the formation of free radicals and increase the resistance to the radiation. Since the position of the net or mesh will be slightly different from day to day, its protective effect will be spread over the treated skin region.

In order to increase the comfort, especially the feeling of safety when taking place on the rather open breast couch, a removable device (28) can be positioned under the breast couch, in order to provide a closure for the open structure of the board or couch and ensure safe positioning of the subject (FIG. 10). Once the patient is correctly positioned and secured, the removable device can be removed, creating the necessary open space for radiation therapy. The removable device (28), has in this case an upper surface structure fitting under the breast board. The shape of the upper surface can be constructed as a docking element that match the bottom-side of the couch. It can be attached to the breast couch, to the patient support system, or can be present on a floor-positioned table, or trolley (29), which can optionally be equipped with a hydraulic arm (30). Alternatively, the breast couch can be lowered onto the removable device (28), avoiding the need of hydraulic systems.

Figure 11:
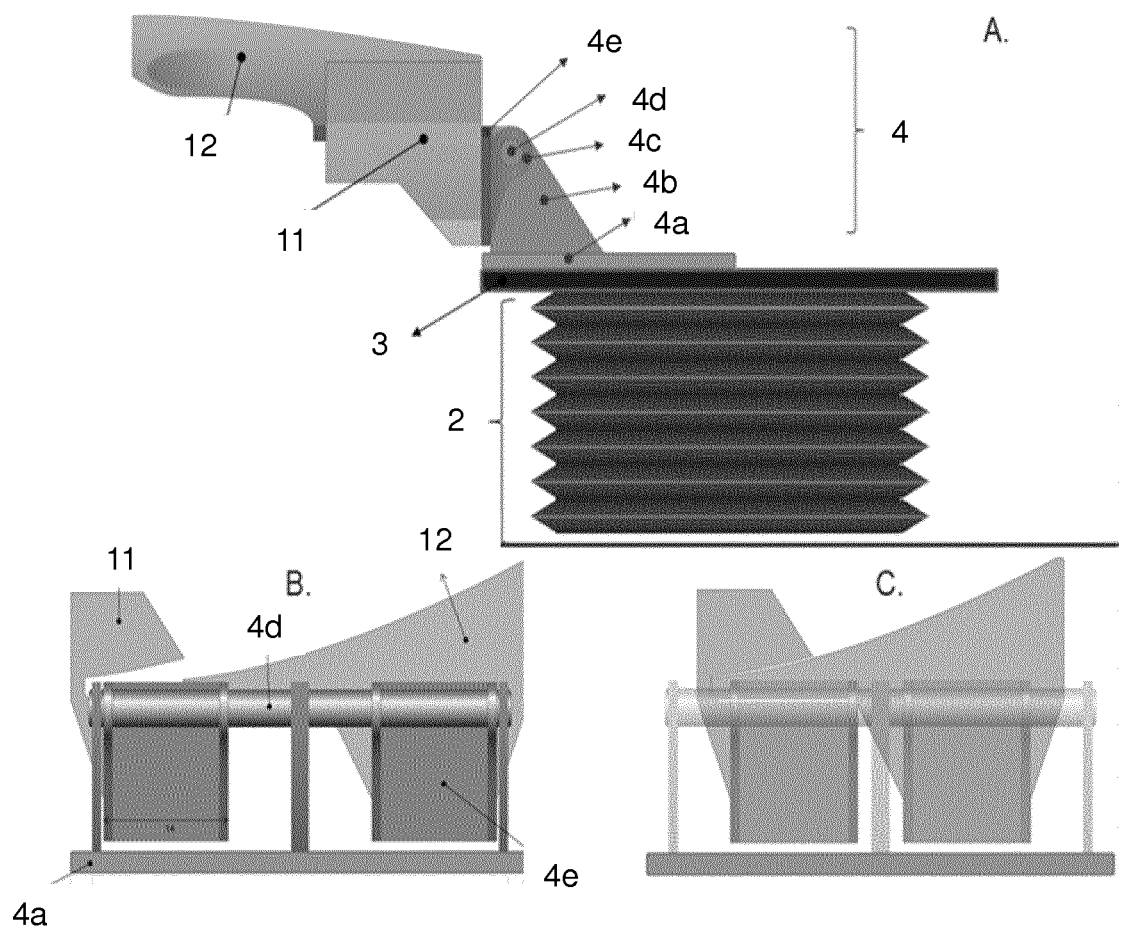
FIG. 11: Shows a schematic view of the anchoring element (4) of one embodiment of the radiotherapy board or couch as defined herein. Panel A: lateral view showing the positioning of the anchorage element with respect to the posterior part of the couch blade. The anchorage element allows varying the separation between arm and body supports to adjust to variations in body size; Panel B: posterior view of the body and arm supports (partially shown) in widest position; Panel C: posterior view of narrowest position; pedestal (2); couch blade (3); arm support (11); a body supporting member (12); anchoring element (4), comprising a base plate (4*a*), a frame (4*b*), a connector structure (4*e*); a bearing (4*c*) on said connector structure and a width regulatory axis (4*d*).

The breast board or couch can be connected to a table top, frame or blade via an anchoring system. In some embodiments like the one shown in FIG. 11, such an anchoring system, structure, or element (4) may comprise a base plate (4a), which can e.g. be attached to the table blade or the pedestal; a frame (4b) substantially perpendicular to the base plate, which can comprise a pivoting means such as a hinge or bearing (4c), and which is connected to one or more connector structure(s) (4e), each carrying one of the body supporting means (12, 13) and the arm supporting means (11). Said frame and connector structure(s) able to slide or translate over a width regulatory rod or axis (4d) (cf. FIG. 11). A schematic representation of such a possible anchorage element is shown in FIG. 11. Panel A shows its position with respect to the posterior part of the couch blade. The anchorage element allows varying the separation between arm (11) and body supports (12 and 13 (not shown)) to adjust to variations in body size. The widest and narrowest separations are shown in panels B and C of FIG. 11. The pivoting means or bearing (4d) makes it possible to tilt the breast board and its body and arm supporting members such that the subject can take place on it in an easy way. The pivoting means or bearing (4d) can also be used to make small position adjustments of the breast board.

In one embodiment, a modular breast board or couch is disclosed, comprising a body support (12 and 13 (not shown)), which supports head, hemi-thorax, contra-lateral breast, contralateral arm and upper abdomen); an ipsilateral arm and shoulder support (11); a lower abdomen and upper leg support (14, 15 not shown) and an anchorage element (4). The anchorage element connects the three supports (11; 12 and 13 (not shown); and 15 (not shown)) to the pedestal, the couch blade, frame, or part thereof. The lower legs and feet can adequately be supported by standard commercial devices or cushions. The anchorage element (4) can furthermore host actuators for tilt and roll control of the patient, which are expected to decrease set-up time and improve precision.

It will be readily apparent to the skilled person that the exemplified embodiments herein should not be interpreted as limiting the scope of the invention. The skilled person would be able to envisage alternatives which would fall within the spirit and scope of the invention.

EXAMPLES

Figure 12:
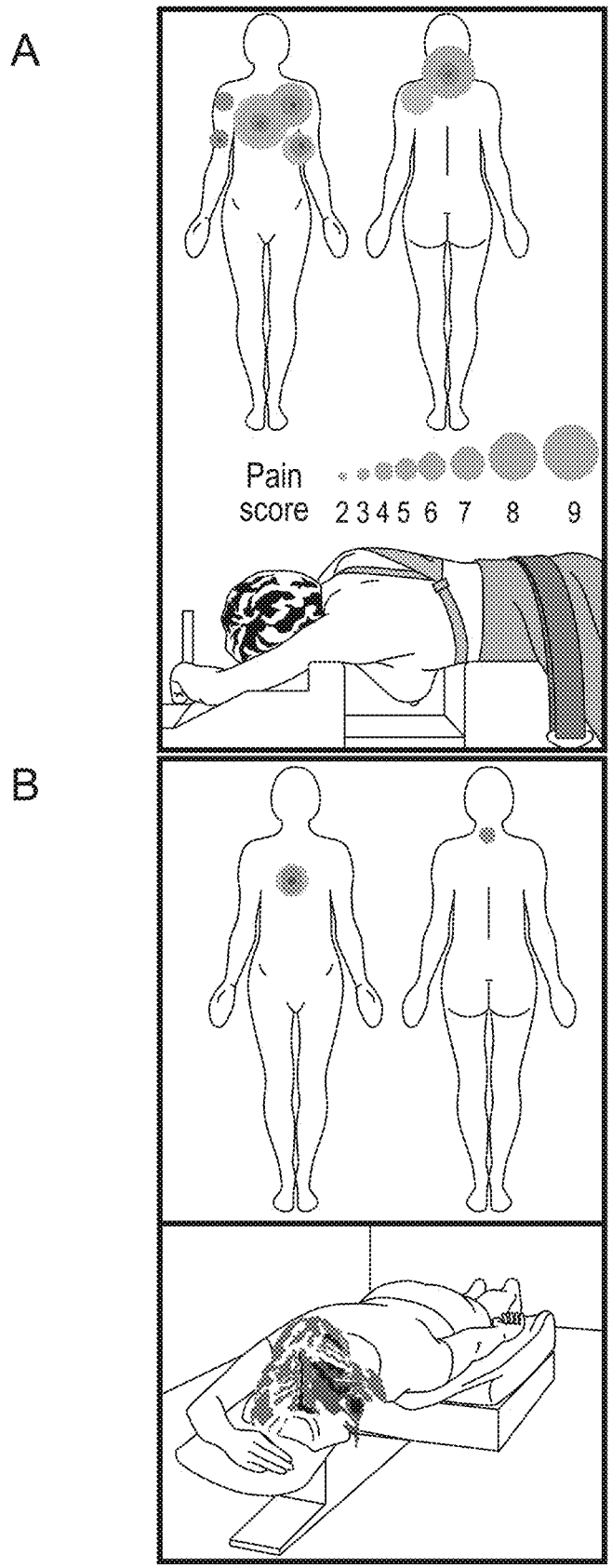
FIG. 12: Pain score in test subjects (n=9) using a reference radiotherapy couch or board (A) and the couch as defined herein (B). Grey circles represent pain: center indicates the anatomical location; radius is proportional to severity of pain score; number of overlapping circles indicates the number of volunteers/patients (n=9) experiencing pain at the indicated location.

Example 1: Iterative Optimisation of the Crawl Position on the Breast Board/Couch Prototype as Defined Herein and its Effect on Pain in the Test Subjects Volunteers and patients were asked to score pain when lying on a reference radiotherapy couch and on the breast board or couch as defined herein. The results were depicted in FIG. 12, wherein the number of patients indicating pain in a certain region is indicated by the size of a circle on said respective spot in the subject's body. The top panel represents the AIO® board from Orfit, while the lower panel represents the prototype of the radiotherapy breast board as defined herein. Much lower pain scores and less painful regions were obtained using the prototype as defined herein. There is a clear observation of significantly improved comfort as compared to the standard breast board.

Figure 13:
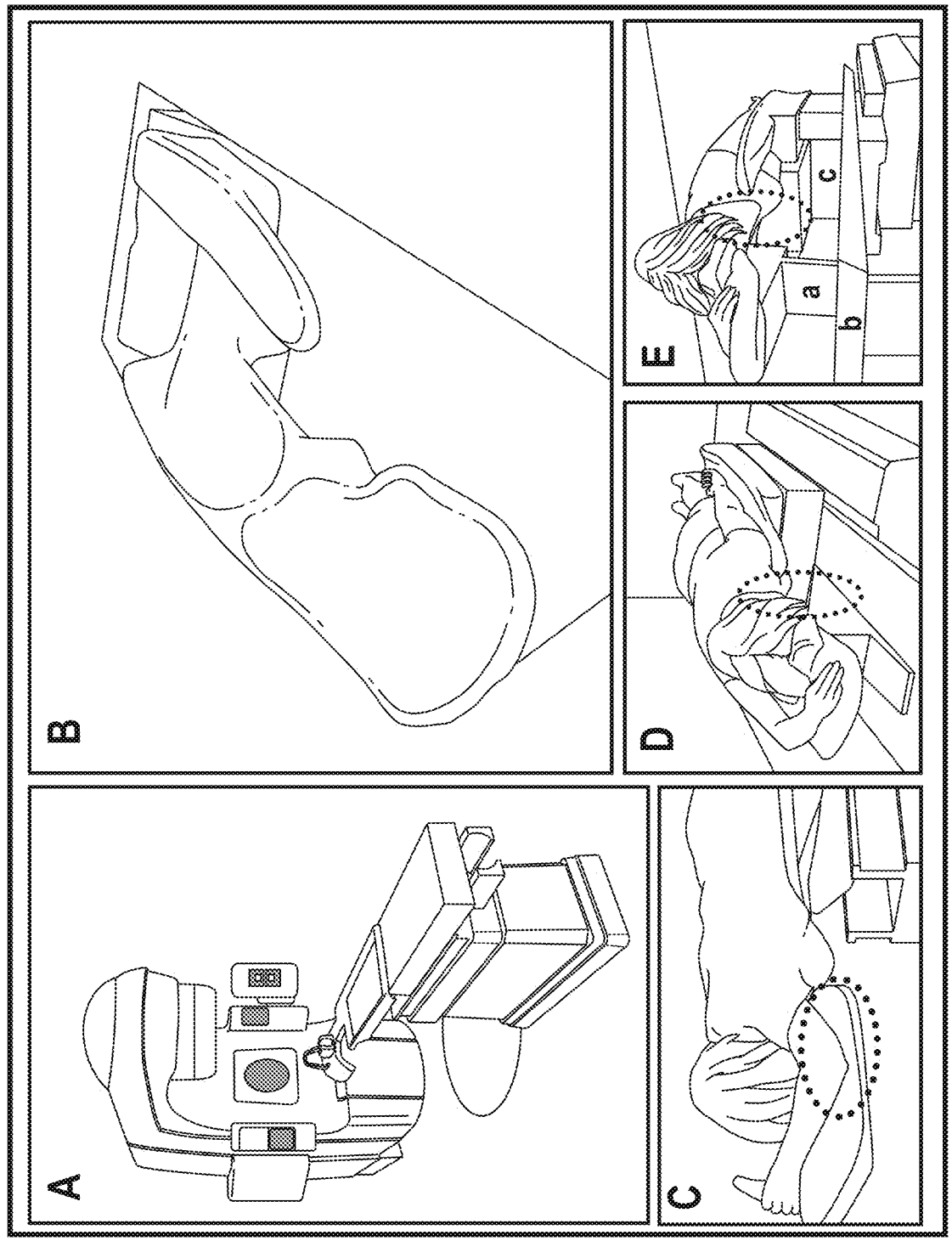
FIG. 13: Indication of the free beam access of a reference table (left panels A and C) and the breast couch or table as defined herein (right top panel (B) and middle (D) and right (E) lower panels). The dotted circle indicates the beam access region.

Example 2: Unobstructed Beam Access Range of Reference Table Vs. Breast Board/Couch Prototype as Defined Herein CT-simulation of cadavers confirmed the utility of unobstructed beams from cranial and anterior directions to avoid lung during LNI. Visual inspection with volunteer and cadaver studies showed coronal (panoramic) beam access range to the pending breast over more than 180° (cf. FIG. 13). In the upper left panel (A) of FIG. 13, a reference table (Varian Pivotal® couch) is anchored to the caudal part of the couch blade. Both upper surfaces of table and couch are horizontally aligned. The right upper panel (B) shows the breast couch or board as defined herein which is elevated above the caudal couch blade though an anchorage element (4) (cf. c) in FIG. 13) to improve patient comfort. In the lower panels, a test subject is placed on either couch and the radiation beam access range is determined. The lower left panel (C) shows a lady positioned on the Pivotal® couch showing that beams from cranial and anterior direction would traverse the arm and parts of the couch (encircled by a dotted line) before reaching axillar or peri-clavicular lymph nodes. The middle (D) and right (E) lower panels show a volunteer positioned on the radiotherapy couch or board as defined herein showing unobstructed beam access from cranial and anterior directions. The right lower panel gives an idea of the angular range in the coronal plane of unobstructed beam access to the breast which can be exploited for dose-painting. A device constructed as a radiotherapy board (B-prototype) is shown, i.e. said board is positioned on an existing radiotherapy couch. When constructed as a radiotherapy couch (C-prototype), the cranial part of the couch blade (a) and the support structure (b) will be removed which will further increase the range of unobstructed beam access. A C-prototype radiotherapy couch would be connected to the caudal part of the couch blade by an anchorage element (c) only.

Figure 14:
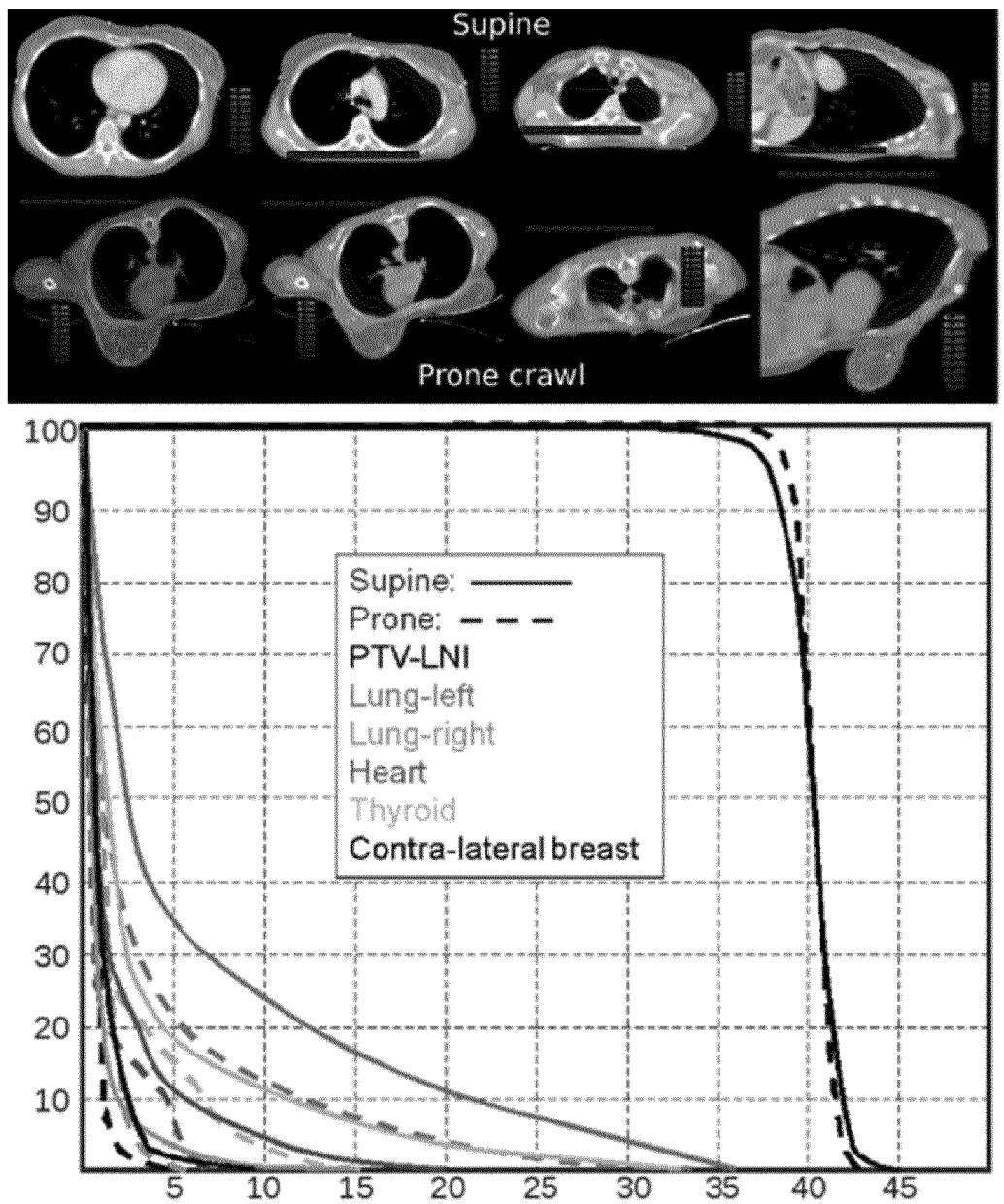
FIG. 14: Shows dose distributions and dose-volume in supine versus crawl prone position. Patients eligible for left-side whole-breast irradiation (WBI) and lymph node irradiation (LNI) were planned in supine position (dose distributions shown in upper panel) and in prone position (dose distributions shown in middle panel). The lower panel shows dose-volume histograms for the planning target volume of lymph node irradiation (PTV-LNI); left lung (Lung-left); right lung (Lung-right); heart, thyroid and contra-lateral breast. The dotted lines indicate the dose-volume histograms in the respective organs using the radiotherapy breast board as defined herein, while the full lines indicate those observed using a reference table in supine position.

Example 3: Dose Distribution in Prone Crawl Positioning of Patients on the Breast Board/Couch as Defined Herein Vs. Reference Supine Positioning Ethical Committee (EC) approval was obtained for using the reference prototype to CT-simulate 10 patients who were referred for left-sided WBI+LNI. Patients are CT-scanned in standard supine position and in prone crawl position. Intensity-Modulated Radiation Therapy (IMRT) plans are made for each position. For the supine position, the standard planning class solution is applied. The results represented in FIG. 14 show that using the radiotherapy board or couch as defined herein offers significant advantages for selecting beam directions that allow heart and lung sparing. Dose distributions in crawl position (middle panel) show tighter conformality than those in supine position (upper panel). Dose-volume histograms (lower panel) show a strong reduction in ipsilateral lung dose yielding values of radiation energy deposition which—for prone crawl—are about half of those for standard supine. Furthermore, the benefit of prone crawl is not limited to ipsilateral lung. Dose indices for the targets of lymph nodes, treated breast (not shown in FIG. 14) heart, contralateral lung, contralateral breast and thyroid are also better for prone crawl position. Such simultaneous improvement of various parameters suggests a systematic origin and not merely a result of Pareto optimality in which a gain in one volume-of-interest would be obtained by losses in other volume(s)-of-interest.

In-silico tests using CT-scanned patients and cadavers confirm the hypothesis that crawl positioning using the radiotherapy board or couch as defined herein opens a window for significant dose-reductions to lungs and other organs at risk.

The invention claimed is:

1. A radiotherapy breast couch for supporting a patient in need of breast tumor radiotherapy in a prone position, the patient having a treated side at which is located a breast and regional lymph nodes undergoing treatment and an opposite, non-treated side at which is located a contralateral breast comprising:
   a longitudinal body supporting member, configured for supporting the non-treated side of the patient's body, including the contralateral breast, comprising an anchorage structure for connecting the body supporting member to a radiotherapy couch, pedestal or robotic arm, and a head support, configured to support the head of the patient;
   a longitudinal first arm supporting member, configured for supporting an ipsilateral arm of said patient at the treated side of the patient, when said ipsilateral arm is held backwards, alongside the body; and
   a second arm supporting member attached to the body supporting member or the head support, configured to support an arm of the patient at the non-treated side;
   wherein said first arm support is positioned parallel to the body supporting member extending in a caudal-cranial direction, wherein said first arm support is not connected to said head support, and wherein the body supporting member and the first arm supporting member are mutually arranged to provide an air gap therebetween for protrusion of the breast undergoing treatment therethrough and for access to the regional lymph nodes undergoing treatment while said patient lies prone on said breast couch,
   wherein the regional lymph nodes comprise at least one of axillary, internal mammary, infraclavicular and supraclavicular lymph nodes neighboring the breast undergoing treatment.

2. The radiotherapy breast couch according to claim 1, wherein said first arm supporting member and body supporting member are connected through said anchorage structure, enabling a separation between said first arm supporting member and body supporting members to be adjusted according to variations in body size.

3. The radiotherapy breast couch according to claim 1, wherein said first and second arm supporting members are configured to support the arms of the patient when in crawl, or skeleton position.

4. The radiotherapy breast couch according to claim 1, wherein the position of said first arm supporting member can be adjusted longitudinally, laterally, and/or vertically.

5. The radiotherapy breast couch according to claim 1, wherein a position of said second arm supporting member can be adjusted longitudinally, laterally, and/or vertically.

6. The radiotherapy breast couch according to claim 1, wherein the first arm supporting member has an inclination of between 0 and 35 degrees with respect to the body supporting member.

7. The radiotherapy breast couch according to claim 1, further comprising a face-mask configured to fixate the head of the patient.

8. The radiotherapy breast couch according to claim 1, wherein said body supporting member is self-supporting and connected to a patient-support system.

9. The radiotherapy breast couch according to claim 1, wherein said body supporting member and/or first arm supporting member is supported by one or more frame members connected via a pivot bearing to said anchorage structure at a first end and to the head support at a second end.

10. The radiotherapy breast couch according to claim 1, wherein said breast couch can be tilted upwards with respect to the anchorage structure and/or a patient support system to which it is connected, in order to facilitate the patient climbing on the breast couch.

11. A removable patient supporting device configured to fit under the radiotherapy breast couch according to claim 1, to facilitate the patient's positioning on the breast couch, wherein said patient supporting device is positioned under the air gap formed by said body supporting member and the first arm supporting member.

12. The radiotherapy breast couch according to claim 1, additionally comprising a mesh or net between the head support and the first arm supporting member, to ensure safe positioning of the patient on said breast couch.

13. The radiotherapy breast couch according to claim 1, which is connected to a table top, frame or blade via an anchoring system comprising: a base plate attached to said table top, frame or blade; an anchoring system frame substantially perpendicular to the base plate and connected thereto; and one or more connector structure(s) each carrying one of the body supporting member and the first arm supporting member and each being connected to said anchoring system frame through a width regulatory rod or axis.

14. The radiotherapy breast couch according to claim 13, wherein said anchoring system frame and said connector structure(s) can slide or translate sideward over said width regulatory rod or axis, enabling the adjustment of a width of the breast couch, or a space between the first arm supporting member and the body supporting member.

15. The radiotherapy breast couch according to claim 1, further comprising a patient-specific, thermoplastic face-mask configured to fixate the head of the patient.

16. A removable patient supporting device configured to fit under the radiotherapy breast couch according to claim 1, to facilitate the patient's positioning on the breast couch, wherein said patient supporting device is positioned under the air gap formed by said body supporting member and said first arm supporting member and on a floor-positioned trolley with a hydraulic arm.

17. A radiotherapy breast board suitable for being placed on, or attached to, a table top, frame, or blade of a radiotherapy or imaging table or couch, for supporting a patient in need of breast tumor radiotherapy in prone position, the patient having a treated side at which is located a breast and regional lymph nodes undergoing treatment and an opposite, non-treated side at which is located a contralateral breast, comprising:
  a longitudinal body supporting member, configured for supporting the non-treated side of the patient's body, including the contralateral breast, comprising an anchorage structure for connecting the body supporting member to a radiotherapy couch, pedestal, or robotic arm;
  a head support, configured to support a head of the patient;
  a longitudinal first arm supporting member, configured for supporting an ipsilateral arm of said patient at the side of treatment of the patient, when said ipsilateral arm is held backwards, alongside the body; and
  a second arm supporting member attached to the body supporting member or head support, configured to support an arm of the patient at the non-treated side;
  wherein said first arm supporting member is positioned parallel to the body supporting member extending in a caudal-cranial direction, wherein said first arm supporting member is not connected to said head support, and wherein the body supporting member and the first arm supporting member are mutually arranged to provide an air gap for protrusion of the breast undergoing treatment there through and for access to the regional lymph nodes undergoing treatment, while said patient lies in prone position on said breast board,
  wherein the regional lymph nodes comprise at least one of axillary, internal mammary, infraclavicular and supraclavicular lymph nodes neighboring the breast undergoing treatment.

18. The radiotherapy breast board according to claim 17, wherein said first arm supporting member and said body supporting member are connected through said anchorage structure, enabling varying a separation between said first arm supporting member and said body supporting members to adjust to variations in body size.

19. The radiotherapy breast board according to claim 17, wherein said first and second arm supporting members are configured to support the arms of the patient when in crawl or skeleton position;
  wherein a position of said first arm supporting member can be adjusted longitudinally, laterally, and/or vertically;
  wherein a position of said second arm supporting member can be adjusted longitudinally, laterally, and/or vertically;
  wherein said first arm supporting member has an inclination of between 0 and 35 degrees with respect to said body supporting member;
  wherein the head of the patient can be fixated by a face-mask.

20. The radiotherapy breast board according to claim 17, wherein said body supporting member is self-supporting and connected to a patient-support system;
  wherein said body supporting member and/or said first arm supporting member is supported by one or more frame members connected via a pivot bearing to said anchorage structure at a first end and to the head support at a second end; or
  wherein said breast board can be tilted upwards with respect to the anchorage structure and/or said patient-support system to which it is connected, in order to facilitate the patients climbing on the breast board.

21. A removable patient supporting device configured to fit under the radiotherapy breast board according to claim 17, to facilitate the patients position on the breast board, wherein said patient supporting device is positioned under the air gap formed by said body supporting member and said first arm supporting member.

22. The radiotherapy breast board according to claim 17, additionally comprising a mesh or net between the head support and the first arm supporting member, to ensure safe positioning of the patient on said board;
  wherein the radiotherapy breast board is connected to a, frame via an anchoring system comprising:
  a base plate attached to said frame;
  said frame substantially perpendicular to the base plate and connected thereto; and
  one or more connector structures each carrying one of the body supporting member and the first arm supporting member and each connector structure being connected to said frame through a width regulatory rod or axis;
  wherein said frame and connector structures can slide or translate sideward over said width regulatory rod or axis, enabling the adjustment of a width of the board, or a space between the first arm supporting member and the body supporting member.

* * * * *